(12) United States Patent
Naito et al.

(10) Patent No.: US 9,909,950 B2
(45) Date of Patent: Mar. 6, 2018

(54) METHOD AND APPARATUS FOR INSPECTING RESIN SHOCK ABSORBER

(71) Applicant: Mitsubishi Electric Corporation, Chiyoda-ku (JP)

(72) Inventors: Shinya Naito, Chiyoda-ku (JP); Hisashi Furuzawa, Chiyoda-ku (JP); Michio Murai, Chiyoda-ku (JP)

(73) Assignee: Mitsubishi Electric Corporation, Chiyoda-ku (JP)

( * ) Notice: Subject to any disclaimer, the term of this patent is extended or adjusted under 35 U.S.C. 154(b) by 0 days.

(21) Appl. No.: 15/323,593

(22) PCT Filed: May 22, 2015

(86) PCT No.: PCT/JP2015/064720
§ 371 (c)(1),
(2) Date: Jan. 3, 2017

(87) PCT Pub. No.: WO2016/038941
PCT Pub. Date: Mar. 17, 2016

(65) Prior Publication Data
US 2017/0138815 A1 May 18, 2017

(30) Foreign Application Priority Data
Sep. 11, 2014 (JP) .................................. 2014-185158

(51) Int. Cl.
G01M 17/04 (2006.01)
G01M 5/00 (2006.01)
(Continued)

(52) U.S. Cl.
CPC ................. *G01M 5/00* (2013.01); *B66B 5/28* (2013.01); *G01M 13/00* (2013.01)

(58) Field of Classification Search
CPC .............. G01M 5/00; G01N 3/42; G01N 3/40
(Continued)

(56) References Cited

U.S. PATENT DOCUMENTS 4,852,397 A * 8/1989 Haggag .................... G01N 3/42
73/82
5,357,786 A * 10/1994 Lung ........................ G01N 3/42
73/81
(Continued)

FOREIGN PATENT DOCUMENTS

JP 29-5497 8/1954
JP 56-161549 U1 12/1981
(Continued)

OTHER PUBLICATIONS

Written Opinion of the International Searching Authority dated Aug. 25, 2015, issued in PCT Application No. PCT/JP2015/064720 (with English translation).

(Continued)

*Primary Examiner* — Harshad R Patel
*Assistant Examiner* — Octavia Hollington
(74) *Attorney, Agent, or Firm* — Oblon, McClelland, Maier & Neustadt, L.L.P.

(57) ABSTRACT

An inspection method and an inspection apparatus capable of readily determining the necessity of replacement of a resin shock absorber at an elevator inspection location without using a car of a rated weight. First, an indenter is pressed into a resin shock absorber for an elevator. A load of pressing the indenter into the resin shock absorber is released. A physical property value indicative of a repulsive force that causes the indenter to bounce from the resin shock absorber by releasing the load is measured. The necessity of replacement of the resin shock absorber is determined by comparing a result of the physical property value obtained (Continued)

by measuring the repulsive force with a reference value prepared in advance.

16 Claims, 19 Drawing Sheets

(51) Int. Cl.
    *B66B 5/28*     (2006.01)
    *G01M 13/00*     (2006.01)
(58) Field of Classification Search
    USPC ........................................................ 73/11.04
    See application file for complete search history.

(56) References Cited

U.S. PATENT DOCUMENTS

| | | | | |
|---|---|---|---|---|
| 7,380,443 | B2* | 6/2008 | Tsujii | ........................ G01N 3/42 73/81 |
| 7,424,822 | B2* | 9/2008 | Isomoto | .................... G01N 3/42 702/155 |
| 2008/0184807 | A1* | 8/2008 | Nakano | .................... G01N 3/08 73/818 |
| 2008/0226218 | A1* | 9/2008 | Abe | ........................ G01L 1/243 385/13 |
| 2011/0227264 | A1 | 9/2011 | Kieffer | |

FOREIGN PATENT DOCUMENTS

| | | |
|---|---|---|
| JP | 62-113932 A | 5/1987 |
| JP | 6-300070 A | 10/1994 |
| JP | 8-217352 A | 8/1996 |
| JP | 9-43110 A | 2/1997 |
| JP | 9-132362 A | 5/1997 |
| JP | 11-182604 A | 7/1999 |
| JP | 2008-82978 A | 4/2008 |
| JP | 2009-63438 A | 3/2009 |
| JP | 2011-73823 A | 4/2011 |
| JP | 2013-19782 A | 1/2013 |
| JP | 2013-56748 A | 3/2013 |

OTHER PUBLICATIONS

International Search Report dated Aug. 25, 2015, in PCT/JP2015/064720, filed May 22, 2015.

* cited by examiner

FIG.2
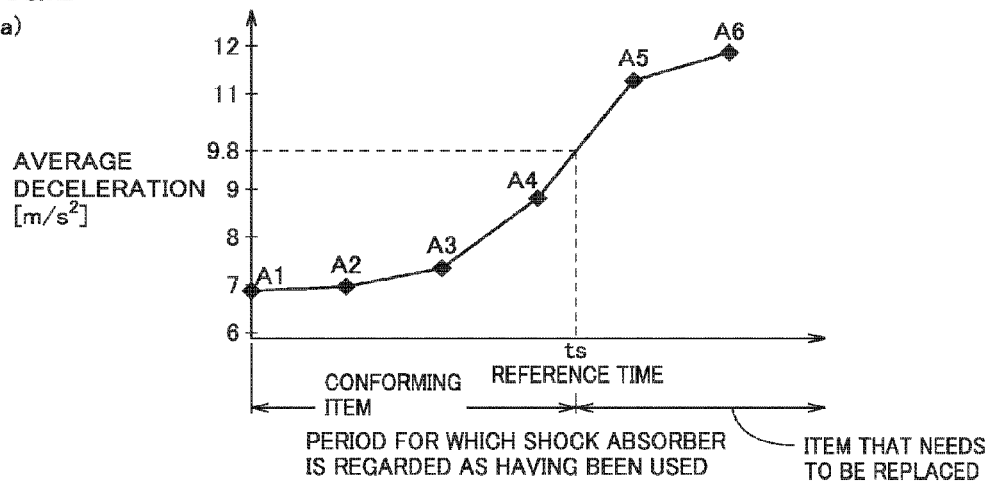
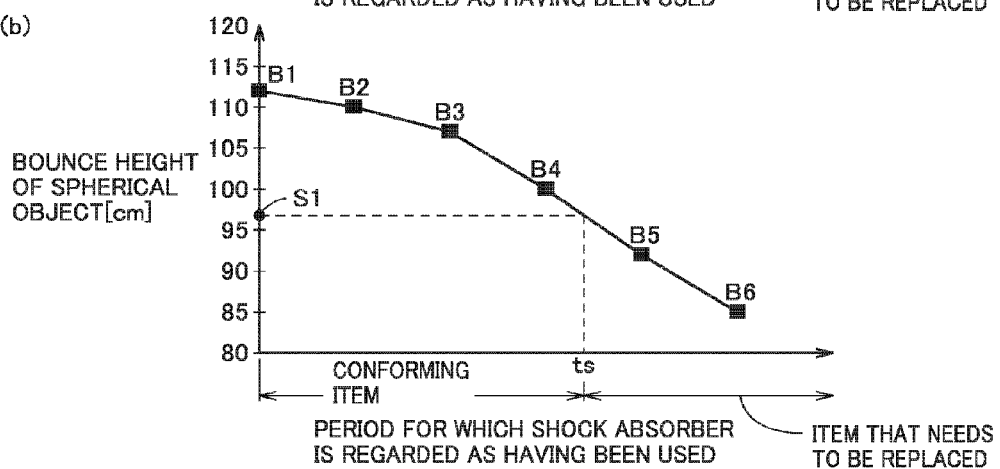
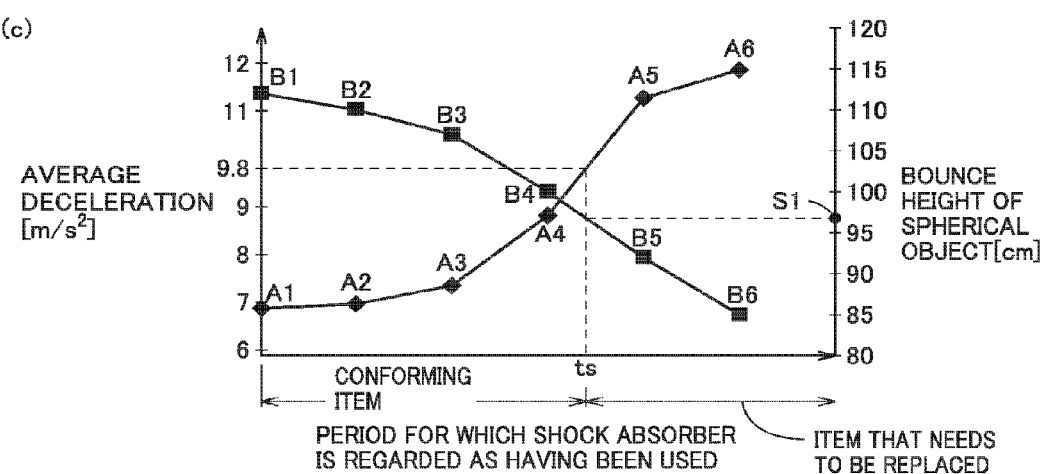

FIG.16
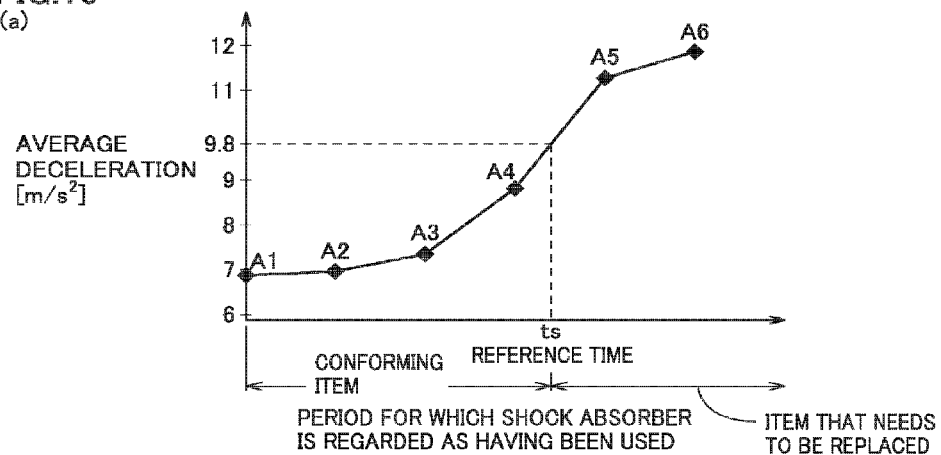
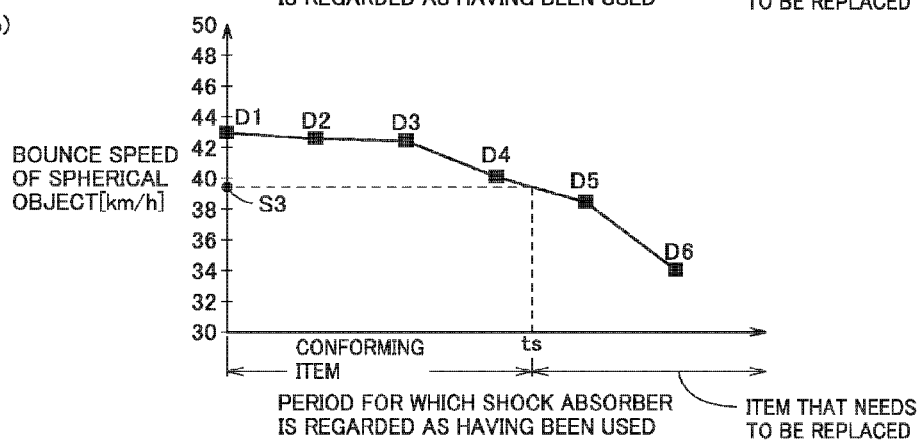
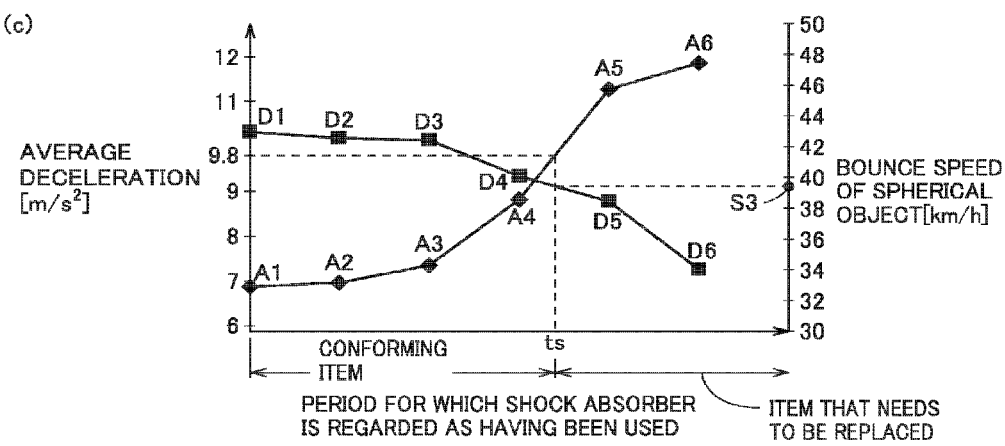

METHOD AND APPARATUS FOR INSPECTING RESIN SHOCK ABSORBER

TECHNICAL FIELD

The present invention relates to methods and apparatuses for inspecting resin shock absorbers, and particularly to a method and an apparatus for inspecting a resin shock absorber for an elevator.

BACKGROUND ART

When an elevator car containing passengers or a balance weight for balancing with the car descends, for some abnormal reason, below the lowest floor of a building and moves down to a pit portion of a hoistway, a shock absorber for an elevator cushions the impact due to collision of the car or balance weight with the pit portion. A spring shock absorber, an oil-filled shock absorber, or a resin shock absorber is used as the shock absorber. The following patent documents each disclose an inspection method or an inspection apparatus for enabling checking of whether or not these shock absorbers have the effect of normally cushioning the impact.

CITATION LIST

Patent Documents

PTD 1: Japanese Patent Laying-Open No. 9-132362
PTD 2: Japanese Patent Laying-Open No. 2013-56748
PTD 3: Japanese Patent Laying-Open No. 9-43110
PTD 4: Japanese Patent Laying-Open No. 62-113932
PTD 5: Japanese Patent Laying-Open No. 6-300070

SUMMARY OF INVENTION

Technical Problem

Among the aforementioned shock absorbers, particularly the resin shock absorber tends to deteriorate due to environment such as temperature and humidity, as compared to the spring shock absorber and oil-filled shock absorber. In other words, as the years pass after installation, the resin shock absorber decreases in its shock absorbing capability to cushion the impact, and sometimes becomes unable to meet the required shock absorbing capability. Another characteristic of the resin shock absorber is that the rate of deterioration, that is, the life, varies with each case, even among items of the same model number, if installation environment varies with each case. Thus, the shock absorbing capability of a resin shock absorber needs to be regularly inspected for each case, and a resin shock absorber that no longer meets the requirements of the regulations or will be unable to meet them after the lapse of a short period of time needs to be replaced by a new one.

In actuality, however, in order to evaluate the shock absorbing capability of a resin shock absorber for each case, it is required to cause a car of a rated weight to collide with the resin shock absorber at a speed corresponding to 115% of a rated speed, and measure a deceleration of the car. Making such a measurement during an inspection of each case of resin shock absorbers at an elevator inspection location is unrealistic in terms of time and effort, cost, and safety. Yet none of the above patent documents discloses a technique of improving such inspection operation.

The present invention has been made in view of the problem described above, and an object of the present invention is to provide an inspection method and an inspection apparatus capable of readily determining the necessity of replacement of a resin shock absorber at an elevator inspection location without using a car of a rated weight.

Solution to Problem

A method for inspecting a resin shock absorber of the present invention includes the following steps.

First, an indenter is pressed into a resin shock absorber for an elevator. A load of pressing the indenter into the resin shock absorber is released. A physical property value indicative of a repulsive force that causes the indenter to bounce from the resin shock absorber by releasing the load is measured. Necessity of replacement of the resin shock absorber is determined by comparing a result of the physical property value obtained by measuring the repulsive force with a reference value prepared in advance.

An apparatus for inspecting a resin shock absorber of the present invention includes an apparatus body, a load applying mechanism, and a measuring mechanism. The apparatus body includes a fixing mechanism for fixing a relative position of a resin shock absorber for an elevator. The load applying mechanism is capable of applying a load of pressing an indenter into the resin shock absorber, and releasing the load. The measuring mechanism measures a physical property value indicative of a repulsive force that causes the indenter to bounce upon release of the load.

Advantageous Effects of Invention

According to the present invention, first, the correlation between a deceleration obtained by a collision test of a resin shock absorber using an elevator car and a physical property value indicative of a repulsive force of an indenter formed of a spherical object or the like is determined, and a reference value of the physical value at a point of time when the resin shock absorber needs to be replaced is determined. Accordingly, during inspections of the resin shock absorber thereafter, the necessity of replacement can be simply determined merely by checking the physical property value indicative of the repulsive force that causes the indenter to bounce without using the car, to maintain a state in which the shock absorber meeting the requirements of the regulations is consistently installed.

BRIEF DESCRIPTION OF DRAWINGS

FIG. 2 is a graph (a) showing relation between a period of use of a resin shock absorber and an average deceleration of a car colliding with the resin shock absorber in the first embodiment; a graph (b) showing relation between the period of use of the resin shock absorber and the bounce height of the indenter formed of a spherical object bouncing from the resin shock absorber in the first embodiment; and a graph (c) combining the above FIGS. 2(a) and 2(b) together.

FIG. 16 is a graph (a) showing relation between a period of use of a resin shock absorber and an average deceleration of a car colliding with the resin shock absorber in the fourth embodiment; a graph (b) showing relation between the period of use of the resin shock absorber and the speed of the indenter formed of a spherical object bouncing from the resin shock absorber in the fourth embodiment; and a graph (c) combining the above FIGS. 16(a) and 16(b) together.

DESCRIPTION OF EMBODIMENTS

Embodiments of the present invention will be described hereinafter with reference to the drawings.

First Embodiment

First, an overview of an inspection method in this embodiment is described with reference to FIG. 1.

Basically, in this embodiment, instead of determining the necessity of replacement of a resin shock absorber 1 by a test of causing an elevator car to collide with resin shock absorber 1, the necessity of replacement of resin shock absorber 1 is determined by pressing an indenter 2 formed of a spherical object into resin shock absorber 1, and measuring a physical property value indicative of a repulsive force indicated by indenter 2 when indenter 2 is released. In this embodiment, the inspection of resin shock absorber 1 is carried out mainly by indenter 2 and a load applying plate 3 (load applying mechanism).

Specifically, referring to FIG. 1(a), first, indenter 2 is placed on the top surface of resin shock absorber 1, and load applying plate 3 is further placed thereon. At this time, indenter 2 and load applying plate 3 may be placed in contact with each other. This is a preparation stage for a step of pressing indenter 2 into resin shock absorber 1.

Resin shock absorber 1 has a circular planar shape, for example, and has a substantially columnar shape as a whole. Resin shock absorber 1 may have a cylindrical shape as a whole, by having a circular hole formed at the center of the top surface as seen in plan view, and having a columnar cavity therein.

Particularly a shock absorbing portion of resin shock absorber 1, which will make contact with an object such as an elevator car and indenter 2, is formed at the top portion of resin shock absorber 1, and is made of urethane foam or rubber, for example. Resin shock absorber 1 is classified as an energy accumulation type nonlinear shock absorber, which is stipulated that about 90% of the total height can be regarded as a stroke. This can reduce the total height of resin shock absorber 1, thereby reducing the depth of a pit portion of a hoistway of the elevator at which resin shock absorber 1 is installed.

It is preferable that indenter 2 have such hardness that it deforms to a negligible extent when pressed into resin shock absorber 1, and have such a shape that does not damage the surface of resin shock absorber 1 when pressed into resin shock absorber 1. It is thus preferable that indenter 2 be made of a metal material such as stainless steel or iron. It is also preferable that particularly a portion of indenter 2 to be pressed into resin shock absorber 1 have a spherical shape or polyhedron shape (cubic shape or regular dodecahedron shape).

Figure 1:
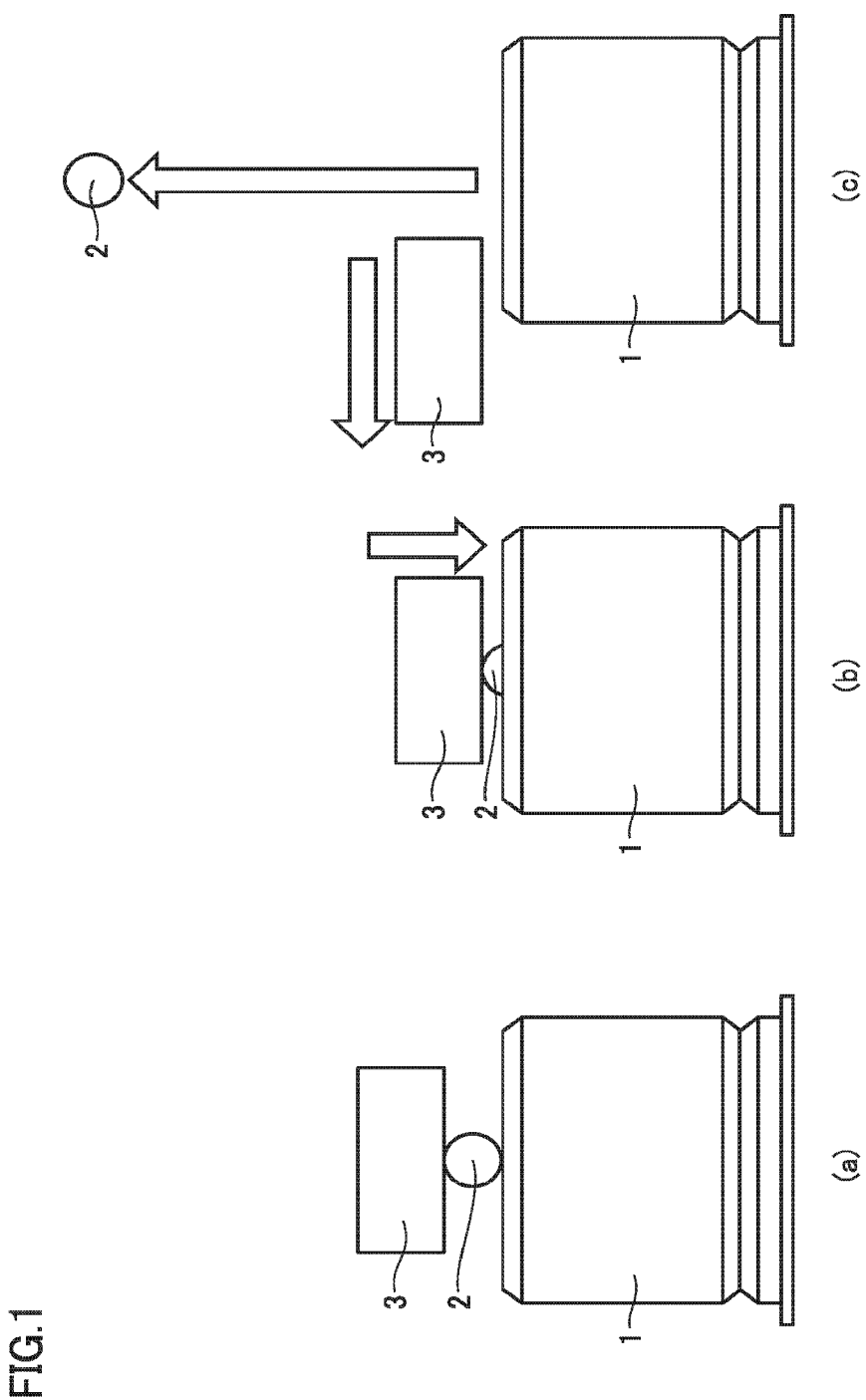
FIG. 1 is a schematic diagram (a) showing a step in a preparation stage for a step of pressing an indenter formed of a spherical object when an inspection apparatus according to a first embodiment is used; a schematic diagram (b) showing the step of pressing the indenter formed of a spherical object when the inspection apparatus according to the first embodiment is used; and a schematic diagram (c) showing a step of causing the indenter formed of a spherical object to bounce and measuring a height thereof when the inspection apparatus according to the first embodiment is used.
Figure 23:
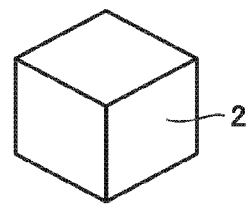
FIG. 23 is a schematic diagram showing a variation of the shape of the indenter, for use in the inspection apparatus according to the first embodiment.

In FIG. 1, indenter 2 is a substantially spherical, small-sized metallic member (iron ball). However, referring to FIG. 23, indenter 2 may have a cubic shape, for example (in this case, one surface forming the cube will be pressed into resin shock absorber 1).

Load applying plate 3 is disposed above indenter 2 to be pressed into resin shock absorber 1 that has been set to an inspection apparatus 100, and can also be disposed directly above indenter 2. This allows application of a load of pressing indenter 2 into resin shock absorber 1. By moving away from a region directly above indenter 2, load applying plate 3 can also release the load that has been applied to press indenter 2 into resin shock absorber 1, thus causing indenter 2 to bounce upward. It is preferable that load applying plate 3 have such hardness, equal to that of indenter 2, that deformation thereof such as a depression and curve that occurs when pressing indenter 2 is small enough to be negligible. It is thus preferable that load applying plate 3 be also made of iron.

Referring now to FIG. 1(b), when load applying plate 3 descends to make contact with the upper surface of indenter 2, load applying plate 3 further moves downward as indicated by a downward arrow in the figure, thus pressing indenter 2 into resin shock absorber 1. Since particularly the shock absorbing portion of resin shock absorber 1 is made of a deformable resin material, the surface thereof is dented and deformed by indenter 2 being pressed therein. Indenter 2 is pressed downward so as to dig into that deformed region of resin shock absorber 1.

Referring now to FIG. 1(c), load applying plate 3 pressing indenter 2 downward moves in a horizontal direction indicated by a leftward arrow in the figure, for example, thus releasing the load of pressing indenter 2 into resin shock absorber 1 in FIG. 1(b). In this embodiment, at this time, indenter 2 is subjected to a repulsive force from resin shock absorber 1 and bounces upward as indicated by an upward arrow in the figure. A height from resin shock absorber 1 that is reached by indenter 2 by this bounce is measured as a physical property value indicative of the repulsive force experienced by indenter 2.

The bounce height of indenter 2 as used herein means a height of movement of indenter 2 due to the repulsive force with respect to the vertical direction from the top surface of resin shock absorber 1 (a height of the highest point that can be reached), where indenter 2 is to bounce in the vertical direction (directly upward direction). That is, in this embodiment, measured as the physical property value (bounce height) is a maximum distance in the vertical direction that can be moved by indenter 2 away from resin shock absorber 1 when indenter 2 bounces from resin shock absorber 1 upon release of the pressing force. A trajectory of the bounce of indenter 2 is depicted substantially directly above the position where indenter 2 is placed on resin shock absorber 1 (a position substantially overlapping the position where indenter 2 is placed on shock absorber 1 as seen in plan view).

This measurement result of the bounce height of indenter 2 is compared with a reference value prepared in advance. As a result, if the measurement result exceeds the reference value, it is determined that resin shock absorber 1 has a high elastic force and a high force of cushioning the impact force, and it is thus determined that resin shock absorber 1 does not need to be replaced. In contrast, if the measurement result falls below the reference value, it is determined that resin shock absorber 1 has a low elastic force and a low force of cushioning the impact force, and it is thus determined that resin shock absorber 1 needs to be replaced.

Referring now to FIG. 2, a description will be given of a method of determining the reference value of the bounce height of indenter 2 at which resin shock absorber 1 needs to be replaced.

First, a single new resin shock absorber 1 to be inspected, or a single used resin shock absorber 1 with a known previous period of use, is prepared as a sample of resin shock absorber 1 for determining the above reference value.

Referring to FIG. 2(a), an elevator car for containing passengers is moved downward to collide with particularly the shock absorbing portion (top portion) of this sample resin shock absorber 1. It is preferable that a speed at which the car is moved down at this time be set to a movable speed of the elevator during descent (a speed slightly higher than a rated speed, for example, a speed corresponding to 115% of the rated speed). An average deceleration of the car upon this collision is measured, which is plotted as indicated by a dot A1 in FIG. 2(a).

Here, the horizontal axis of the graph of FIG. 2(a) represents the period of use of sample resin shock absorber 1. This period of use may be a value of an actual period of use, or a value of a period of use for which resin shock absorber 1 can be regarded as having been used, by subjecting resin shock absorber 1 to an environment in which the temperature rapidly varies repeatedly by a so-called accelerated deterioration test, for example, to intentionally cause deterioration of resin shock absorber 1 (a period for which the shock absorber is regarded as having been used).

The vertical axis the graph of FIG. 2(a) represents the average deceleration of the car upon the above collision. The deceleration as used herein means acceleration that reduces the speed of the car moving downward by the collision, and is indicated as a negative value if downward speed and acceleration are indicated as positive values.

Referring now to FIG. 2(b), resin shock absorber 1 that has been subjected to the measurement of the average deceleration of the car is subjected to a step of pressing indenter 2 into resin shock absorber 1 and releasing indenter 2 in the manner shown in FIG. 1, to measure a height from resin shock absorber 1 of the bounce of indenter 2 with respect to resin shock absorber 1. This is plotted as a dot B1 in FIG. 2(b).

Referring again to FIGS. 2(a) and 2(b), next, deterioration of sample resin shock absorber 1 equivalent to the deterioration after use of resin shock absorber 1 for a prescribed period of time is caused by a so-called accelerated deterioration test, for example, then a dot A2 indicating an average deceleration due to the collision of the elevator car again, and a dot B2 indicating a bounce height of indenter 2 by pressing and releasing indenter 2, are determined. The accelerated deterioration test is conducted on sample resin shock absorber 1 here for the purpose of more efficiently (in a shorter period of time) obtaining sample resin shock absorber 1 that can be regarded as having been used for a longer period of time.

Thereafter, the accelerated deterioration test, and the step of determining the average deceleration of the car and the bounce height of indenter 2 described above are repeated. In other words, the step of determining the average deceleration of the car and the bounce height of indenter 2 described above is performed for a plurality of times while the period of use of resin shock absorber 1 (the period regarded as a period of use by the accelerated deterioration test) is varied. Accordingly, a dot A3 to a dot A6 and a dot B3 to a dot B6 are plotted as shown in FIGS. 2(a) and 2(b), for example. A curve obtained by connecting the dots plotted in each graph indicates relation between the period of use of resin shock absorber 1 (the period regarded as a period of use by the accelerated deterioration test) and the average deceleration of the car (the bounce height of indenter 2).

Referring to FIG. 2(a), and FIG. 2(c) in which the curves in both graphs are overlapped together, a replacement time point to replace this resin shock absorber 1 is determined based on temporal variation in the average deceleration upon collision of the car with resin shock absorber 1.

Here, an energy accumulation type nonlinear shock absorber is required by overseas regulations that a car of a rated weight have an average deceleration of equal to or less than 9.8 m/s$^2$ (about 9.80665 m/s$^2$ to be more exact) when colliding with resin shock absorber 1 at a speed corresponding to 115% of a rated speed (that is, that the car decelerate gradually at a deceleration equal to or less than this deceleration). This gradual deceleration can be implemented by resin shock absorber 1 having high elasticity (resin shock absorber 1 being relatively new).

Thus, from the graphs of FIGS. 2(a) and (c), the average deceleration of 9.8 m/s$^2$ can be set as a value to replace resin shock absorber 1, and a reference time ts when this value is reached can be set as a time to replace resin shock absorber 1 (replacement time point).

Referring to FIGS. 2(b) and (c), a bounce height S1 of indenter 2 from resin shock absorber 1 at this replacement time point ts is determined as the reference value to replace resin shock absorber 1. In FIG. 2(c), bounce height S1 of indenter 2 serving as the reference value to replace shock absorber 1 is about 97 cm.

At each time point of points A1 to A4 and points B1 to B4 at which the (regarded) period of use is shorter than that at replacement time point ts, the average deceleration is equal to or less than 9.8 m/s$^2$ and the bounce height of indenter 2 is equal to or more than 97 cm. Therefore, when the bounce height of indenter 2 measured at an installation location of any resin shock absorber 1 is equal to or more than 97 cm, it can be determined that resin shock absorber 1 does not need to be replaced. In contrast, at each time point of points A5, A6 and points B5, B6 at which the (regarded) period of use is longer than that at replacement time point ts, the average deceleration exceeds 9.8 m/s$^2$ and the bounce height of indenter 2 is less than 97 cm. Therefore, when the bounce height of indenter 2 measured at an installation location of any resin shock absorber 1 is less than 97 cm, it can be determined that resin shock absorber 1 needs to be replaced.

The bounce height of indenter 2 with respect to resin shock absorber 1 as described above varies with the size of indenter 2, the depth to which indenter 2 is pressed downward from the top surface of resin shock absorber 1, and the time between when indenter 2 is pressed downward from the top surface of resin shock absorber 1 and when indenter 2 is released. Thus, it is required that each of the aforementioned parameters (the size of indenter 2, the depth to which indenter 2 is pressed downward, and the time between when indenter 2 is pressed and when indenter 2 is released) have a constant value when obtaining the plot data at point B1 to point B6 in FIGS. 2(*b*) and (*c*) described above, and thereafter when measuring the bounce height of indenter 2 with respect to resin shock absorber 1 at an elevator inspection location. If the pressing can be performed under the same conditions with the constant values as described above, indenter 2 is not limited to being pushed by load applying plate 3 (mechanical mechanism or electrically-powered mechanism installed in the inspection apparatus) as in FIG. 1(*b*), but may be manually pushed, for example.

As the size of indenter 2 increases, a higher load is required when pushing indenter 2 downward from the top surface of resin shock absorber 1, which may result in difficult operation. As the size of indenter 2 decreases, in contrast, a lower load is required when pushing indenter 2 downward from the top surface of resin shock absorber 1, however, the repulsive force after the pressing load is released becomes weaker and the bounce height of indenter 2 becomes smaller, which may result in difficulty in determining the necessity of replacement. The determination of the necessity of replacement of resin shock absorber 1 can be made more accurately with a higher bounce than with a lower bounce of indenter 2. Thus, when consideration is given to both workability and the accuracy of determination of the necessity of replacement, it is preferable to use an iron ball having an outer diameter of equal to or more than 10 mm and equal to or less than 15 mm as indenter 2. However, the size of indenter 2 is not limited as such, and indenter 2 having a diameter beyond the above range may be used. In addition, as will be described later, the size of indenter 2 should sometimes be determined in consideration of a planar shape of the top surface of resin shock absorber 1 on which indenter 2 is placed.

A greater depth to which indenter 2 is pressed downward from the top surface of resin shock absorber 1 allows indenter 2 to bounce higher when the load is released, thus allowing for more accurate determination of the necessity of replacement of resin shock absorber 1. It is preferable that the depth to which indenter 2 is pressed downward from the top surface of resin shock absorber 1 be greater than a value of the radius of indenter 2.

It is preferable that the time between when indenter 2 is pressed and when indenter 2 is released, that is, the time during which indenter 2 is retained in a pressed state as shown in FIG. 1(*b*), be as short as possible. A shorter time allows indenter 2 to bounce higher after the release. The reason for this is believed to be that stress relaxation occurs from the moment indenter 2 is pressed from the top surface of resin shock absorber 1, and the repulsive force that causes indenter 2 to bounce from resin shock absorber 1 decreases with the passage of time.

By way of example, in this embodiment, it is preferable, for example, that the diameter of indenter 2 be 10 mm, the depth to which indenter 2 is pressed downward from the top surface of resin shock absorber 1 be 7 mm, and the time between the start of the pressing of indenter 2 and the release of indenter 2 be one second.

Figure 3:
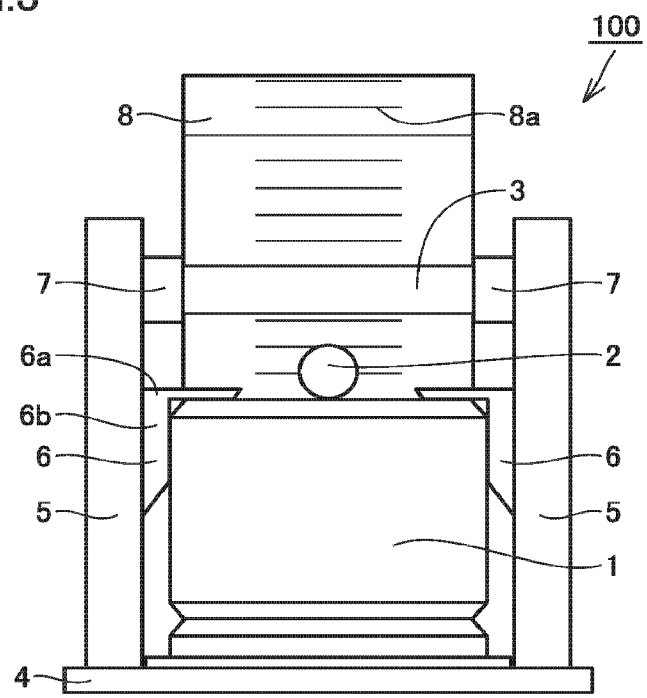
FIG. 3 is a schematic front view showing the configuration of the inspection apparatus according to the first embodiment.
Figure 4:
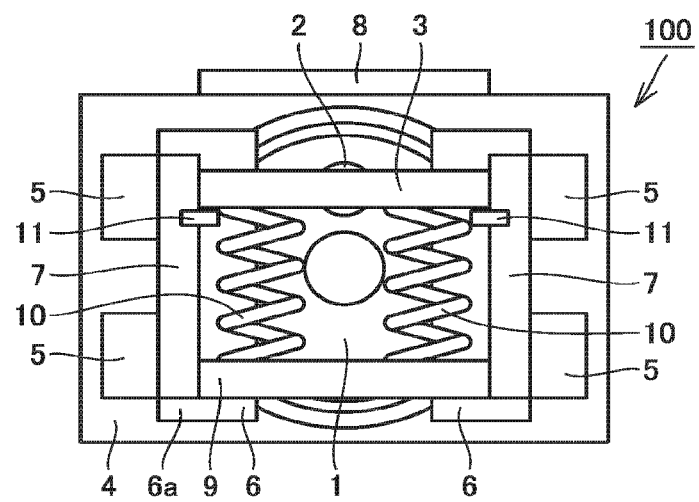
FIG. 4 is a schematic plan view showing the configuration of the inspection apparatus according to the first embodiment.

Referring now to FIGS. 3 and 4, the configuration of the inspection apparatus of the resin shock absorber for an elevator according to this embodiment is described. As FIG. 3 is a front view of inspection apparatus 100, an up-down direction in the figure represents a height direction which is substantially the vertical direction, a right-left direction in the figure represents a width direction of the entire inspection apparatus 100, and a direction perpendicular to the plane of the drawing represents a depth direction of the entire inspection apparatus 100. As FIG. 4 is a plan view of inspection apparatus 100, an up-down direction in the figure represents the depth direction of the entire inspection apparatus 100, the upper side in the figure represents the back side, and the lower side in the figure represents the front side. A right-left direction in FIG. 4 represents the width direction of the entire inspection apparatus 100, and a direction perpendicular to the plane of the drawing represents the height direction (vertical direction).

Referring to FIGS. 3 and 4, inspection apparatus 100 of this embodiment is a device used to determine the necessity of replacement of resin shock absorber 1 for an elevator, by checking whether or not resin shock absorber 1 has the function of cushioning the impact upon collision with an elevator car. This inspection of resin shock absorber 1 using inspection apparatus 100 is carried out mainly by indenter 2 and load applying plate 3 (load applying mechanism) as described above. In the front view of FIG. 3, however, the illustration of a spring fixing plate 9 to be described later is omitted for the purpose of illustration (the same being applied to each front view hereinafter).

Inspection apparatus 100 has an apparatus body including, for example, a base 4, struts 5, shock absorber fixing plates 6, and linear guides 7. Inspection apparatus 100 also has a height display plate 8 (measuring mechanism) with scales 8*a* in the height direction of the bounce of resin shock absorber 1, for measuring a height from resin shock absorber 1 that is reached by indenter 2 bouncing from resin shock absorber 1 during the inspection.

Base 4 is installed at the lowest portion of inspection apparatus 100 as the foundation of the entire inspection apparatus 100, and has a rectangular planar shape, for example. Resin shock absorber 1 as an object to be inspected can be placed on a central portion of base 4.

Struts 5 are columnar members mounted in regions near four corners of the rectangular shape of base 4, for example, and extend along a direction substantially perpendicular to the main surface of base 4, that is, a substantially vertical direction (the direction in which indenter 2 bounces). Although struts 5 have a rectangular planar shape in FIG. 4, this is not limiting.

Shock absorber fixing plates 6 (fixing mechanism) are fixed to struts 5, and have the function of supporting (holding down and fixing) resin shock absorber 1 placed on base 4 from above and from the side. That is, shock absorber fixing plates 6 have the function of determining a position of resin shock absorber 1 relative to the apparatus body of inspection apparatus 100, and fixing resin shock absorber 1 at that position. A pair of shock absorber fixing plates 6 is disposed oppositely with respect to the width direction of inspection apparatus 100, for example, each extending along the depth direction of inspection apparatus 100 (along the horizontal direction) so as to make contact with and be fixed to each of two struts 5 aligned at a distance from one another in the depth direction.

Each of shock absorber fixing plates 6 includes a rectangular first fixing region 6a extending in the depth direction of inspection apparatus 100 (the up-down direction in FIG. 4) as seen in plan view, and a second fixing region 6b intersecting first fixing region 6a, making contact with and being fixed to struts 5, and extending in the depth direction of inspection apparatus 100. With first fixing region 6a being disposed above resin shock absorber 1 and contacting the top portion of resin shock absorber 1, and second fixing region 6b being disposed on the side surface of resin shock absorber 1 and contacting a portion of the side surface of resin shock absorber 1, shock absorber fixing plate 6 pinches and fixes resin shock absorber 1 from two directions, that is, from above and from the side.

With shock absorber fixing plates 6 having the configuration including regions 6a and 6b as described above, shock absorber fixing plates 6 can be readily fixed to struts 5, and shock absorber fixing plates 6 can readily fix resin shock absorber 1 (the relative position thereof) to inspection apparatus 100.

Linear guides 7 are columnar members extending along the depth direction of inspection apparatus 100 (along the horizontal direction) so as to make contact with and be fixed to both of two struts 5 aligned at a distance from each other in the depth direction. Like shock absorber fixing plates 6, a pair of linear guides 7 is disposed oppositely with respect to the width direction of inspection apparatus 100, for example, and is disposed to include a portion of a region directly above each of the pair of shock absorber fixing plates 6.

Disposed between the pair of linear guides 7 disposed at a distance from each other with respect to the width direction of inspection apparatus 100 is load applying plate 3, which is a columnar member extending in a direction (width direction) intersecting the direction in which linear guides 7 extend as seen in plan view. Load applying plate 3 is disposed such that one and the other end portions thereof with respect to the direction in which load applying plate 3 extends are in contact with one and the other of the pair of linear guides 7, respectively.

The pair of linear guides 7 is provided with grooves for grasping the one and the other end portions of load applying plate 3. The grooves allow grasped load applying plate 3 to move along the direction in which linear guides 7 extend (along the horizontal direction).

More specifically, the configuration is as follows. In addition to load applying plate 3, spring fixing plate 9 is disposed between the pair of linear guides 7. Like load applying plate 3, spring fixing plate 9 is a columnar member extending in the right-left direction in FIGS. 3 and 4, that is, the width direction of inspection apparatus 100, for example. Thus, spring fixing plate 9 is disposed between the pair of linear guides 7 so as to be along (so as to be aligned substantially parallel to) the direction in which load applying plate 3 extends. Unlike load applying plate 3, however, spring fixing plate 9 is not configured so as to be able to move along the depth direction in which linear guides 7 extend. Each of opposite end portions of spring fixing plate 9 is fixed to each of the pair of linear guides 7 at one end portion of each linear guide 7 (the lower side in FIG. 4, that is, the end portion on the front side of inspection apparatus 100).

Movement of load applying plate 3 along linear guides 7 is made by extension and contraction of springs 10 disposed between load applying plate 3 and spring fixing plate 9. That is, springs 10 (for example, two springs 10 at a distance from each other) are disposed so as to extend along the direction in which linear guides 7 extend, each having one end portion fixed to a portion of the surface of load applying plate 3 and the other end portion fixed to a portion of the surface of spring fixing plate 9. Thus, load applying plate 3 is coupled to spring fixing plate 9 by springs 10. Since spring fixing plate 9 is fixed with respect to the apparatus body of inspection apparatus 100, load applying plate 3 can move along linear guides 7 in position relative to the apparatus body, in accordance with the extension and contraction of springs 10 disposed so as to extend along the direction in which linear guides 7 extend.

With load applying plate 3 grasped by linear guides 7 moving along the direction in which linear guides 7 extend in this manner, it is possible to dispose indenter 2 directly below load applying plate 3 and apply a load of pressing indenter 2 by load applying plate 3, or to dispose load applying plate 3 in a region other than the region directly above indenter 2 and release the load of pressing indenter 2.

As shown particularly in FIG. 4, it is preferable that load applying plate 3 be fixed with respect to the apparatus body, by stoppers 11 provided to engage with a portion of linear guides 7, so as not to move in position relative to the apparatus body with springs 10 maintained in an extended state.

Linear guides 7 can also move in position relative to the apparatus body along the vertical direction in which struts 5 extend. The pair of adjacent struts 5 with respect to the right-left direction in FIG. 4 is provided with grooves for grasping linear guides 7. The grooves allow grasped linear guides 7 to move along the direction in which struts 5 extend (along the vertical direction in which indenter 2 bounces). This in turn allows load applying plate 3 grasped by linear guides 7 to move along the direction in which struts 5 extend (along the vertical direction in which indenter 2 bounces). With the movement of linear guides 7 in the vertical direction, spring fixing plate 9 fixed thereto can also move together with linear guides 7 with respect to the vertical direction.

With load applying plate 3 grasped by linear guides 7 moving along the direction in which struts 5 extend in this manner, it is possible to bring load applying plate 3 into contact with indenter 2 directly therebelow to press indenter 2 downward, or to move load applying plate 3 away from indenter 2 directly therebelow (to release the load of pressing indenter 2 downward).

Figure 5:
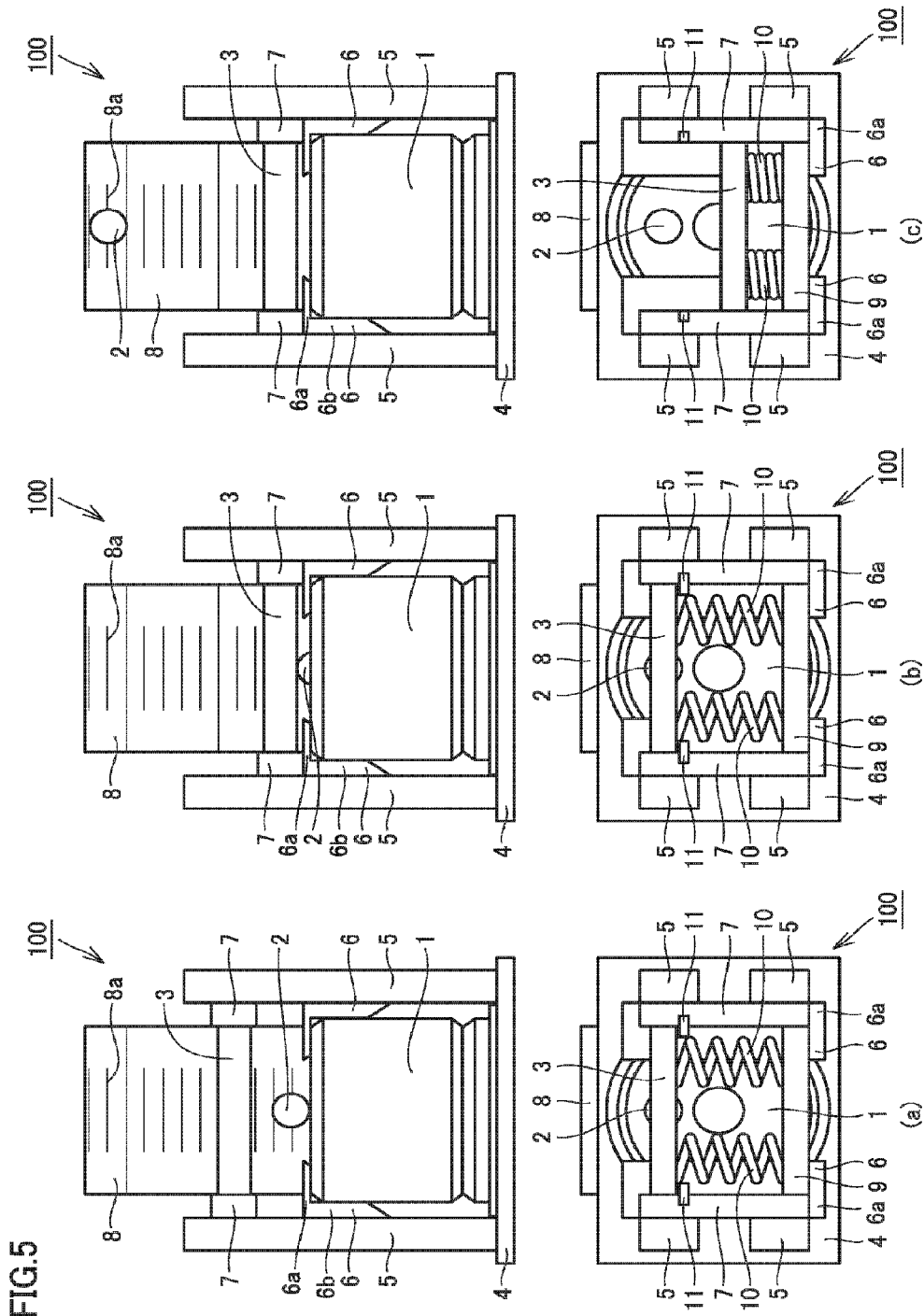
FIG. 5 is a schematic front view and a schematic plan view (a), corresponding to the state of FIG. 1(a), showing an aspect of each member in the preparation stage for the step of pressing the indenter formed of a spherical object when the inspection apparatus according to the first embodiment is used; a schematic front view and a schematic plan view (b), corresponding to the state of FIG. 1(b), showing an aspect of each member in the step of pressing the indenter formed of a spherical object when the inspection apparatus according to the first embodiment is used; and a schematic front view and a schematic plan view (c), corresponding to the state of FIG. 1(c), showing an aspect of each member in the step of causing the indenter formed of a spherical object to bounce and measuring the height thereof when the inspection apparatus according to the first embodiment is used.

Referring now to FIG. 5, the operation of each member in the inspection step of resin shock absorber 1 using inspection apparatus 100 of FIGS. 3 and 4 is described.

Referring to FIG. 5(a), the upper diagram is a schematic front view of the entire inspection apparatus 100, and the lower diagram is a schematic plan view of the entire inspection apparatus 100 (the same being applied to FIGS. 5(b) and (c) to be described later). Resin shock absorber 1 is placed on base 4 of the body of inspection apparatus 100, and held down and fixed from above and from the side by shock absorber fixing plates 6 serving as a fixing mechanism. Indenter 2 is placed on the top surface of resin shock absorber 1.

If resin shock absorber 1 has a cylindrical shape, for example, a hole is formed in a portion (particularly a central portion) of its top surface where a cylindrical cavity portion is to be formed, so the top surface will have an annular planar shape. In this case, since indenter 2 is placed on this annular portion, it is preferable to determine the size of indenter 2 in consideration of the width, which intersects the circumference, of the above annular portion of resin shock absorber 1 (such that the diameter will be smaller than the width).

For example, load applying plate 3 moves along the direction in which linear guides 7 extend to a position where springs 10 extend to the fullest extent (the distance between load applying plate 3 and spring fixing plate 9 reaches its maximum distance), at which point load applying plate 3 is fixed to (the apparatus body including) linear guides 7 by stoppers 11 so as to suppress the movement of load applying plate 3 with respect to the direction in which linear guides 7 extend. At this point of time, load applying plate 3 is disposed at a position away from and above the top surface of resin shock absorber 1. In addition, at this point of time, load applying plate 3 is disposed directly above indenter 2.

Referring to FIG. 5(*b*), load applying plate 3 directly above indenter 2 moves downward together with spring fixing plate 9 along the direction in which struts 5 (grasping linear guides 7) extend, resulting in contact between load applying plate 3 and indenter 2. Load applying plate 3 in contact with indenter 2 in this manner further moves downward along the extension direction of struts 5 grasping linear guides 7, causing indenter 2 in contact with load applying plate 3 to be pressed into resin shock absorber 1 therebelow.

At this time, it is preferable to move shock absorber fixing plates 6 down to a position at which linear guides 7 make contact with a surface of first fixing region 6*a*, for example, of shock absorber fixing plates 6 directly therebelow. By so doing, shock absorber fixing plates 6 are fixed to struts 5 and do not move, thereby allowing for a constant amount of descent of load applying plate 3 during each measurement. Accordingly, the depth to which indenter 2 is pressed downward through the top surface of resin shock absorber 1 by load applying plate 3 can be made constant during each measurement.

Referring to FIG. 5(*c*), stoppers 11 are removed while the state in which indenter 2 is pressed downward is maintained. If springs 10 contract at this time by the elastic force, load applying plate 3 is drawn in the horizontal direction (toward spring fixing plate 9) along the direction in which linear guides 7 extend, and moves in position relative to the apparatus body. Accordingly, indenter 2 is released from load applying plate 3, and thus bounces upward by a repulsive force due to the pressing of resin shock absorber 1 downward.

This bounce height of indenter 2 with respect to the top surface of resin shock absorber 1 is confirmed with scales 8*a* of height display plate 8. This bounce height can be read visually, or from a video recording result.

The function and effect of this embodiment will now be described.

In this embodiment, by preparing the data of FIG. 2 in advance, the necessity of replacement of resin shock absorber 1 can be readily determined thereafter merely by measuring the physical property value (bounce height) indicative of the repulsive force exerted on indenter 2 by resin shock absorber 1, without applying the impact force to resin shock absorber 1 using the elevator car.

Replacement time point ts indicative of the time when the replacement is needed varies, even among resin shock absorbers 1 of the same model number, with the installation environment such as temperature and humidity. However, at least that the average deceleration is 9.8 m/s$^2$ and the bounce height of indenter 2 is 97 cm at replacement time point ts remains substantially the same among resin shock absorbers 1 of the same model number, regardless of the installation environment such as temperature and humidity. Accordingly, once the data of FIG. 2 is obtained, during inspections of resin shock absorber 1 at an elevator inspection location thereafter, the necessity of replacement of resin shock absorber 1 can be determined merely by determining whether or not the above bounce height is equal to or greater than a reference value S1, that is, 97 cm, by using extremely small indenter 2 and inspection apparatus 100 as compared to an elevator car, without using an elevator car. Thus, regardless of the installation environment of an elevator inspection location, the shock absorbing capability of resin shock absorber 1 can be simply determined using the data of FIG. 2, without performing an impact test using the car at the inspection location.

Moreover, with the inspection method and inspection apparatus 100 of this embodiment, an initial test for detective resin shock absorbers 1 can also be simply performed.

By using the height from resin shock absorber 1 that is reached by bouncing indenter 2 as the physical property value indicative of the repulsive force that causes indenter 2 to bounce as in this embodiment, the measurement can be extremely readily made merely by using height display plate 8.

The steps of pressing indenter 2 into resin shock absorber 1 and releasing indenter 2 as in this embodiment can be readily implemented by the configuration in which load applying plate 3 can press indenter 2 by moving along struts 5, and load applying plate 3 can release indenter 2 from resin shock absorber 1 by moving in the direction in which linear guides 7 extend while maintaining the pressed indenter 2, as described above.

Second Embodiment

Figure 6:
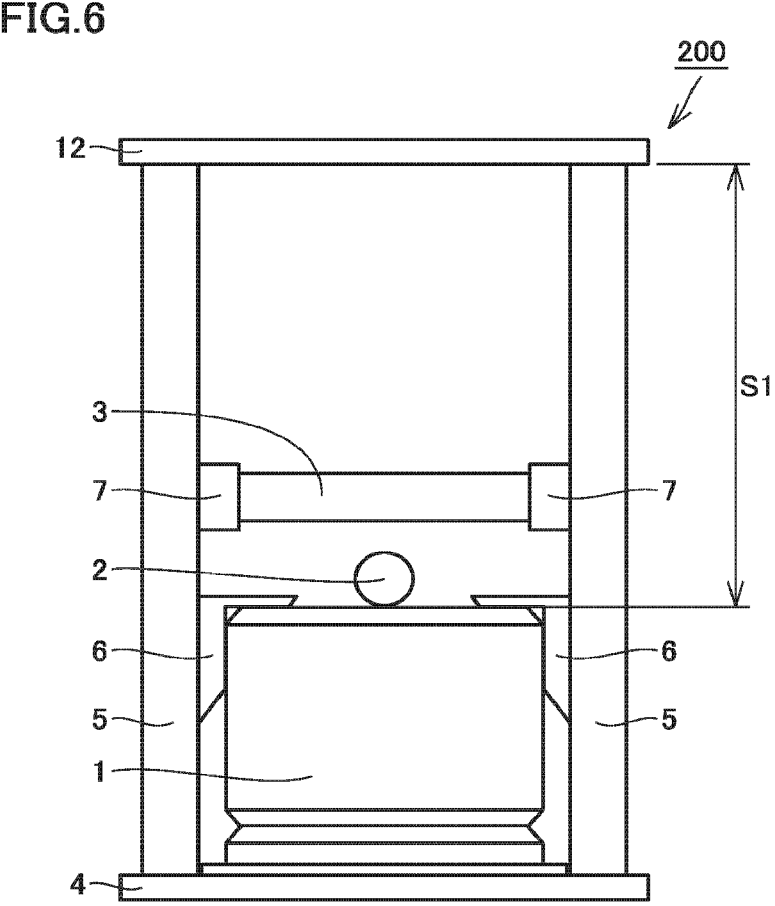
FIG. 6 is a schematic front view showing the configuration of an inspection apparatus according to a second embodiment.
Figure 7:
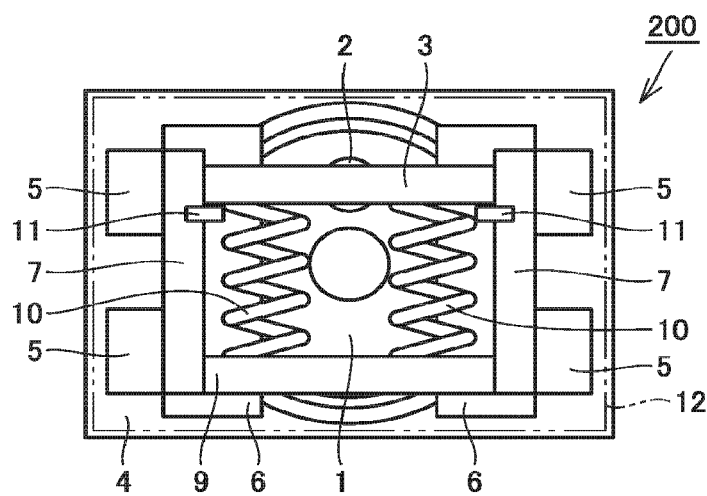
FIG. 7 is a schematic plan view showing the configuration of the inspection apparatus according to the second embodiment.

Referring to FIGS. 6 and 7, an inspection apparatus 200 of this embodiment basically has the same configuration as that of inspection apparatus 100 of the first embodiment, but is different from inspection apparatus 100 in that it has a height reference plate 12 as the measuring mechanism above load applying plate 3.

Height reference plate 12 is disposed such that its height from the top surface of resin shock absorber 1 placed on inspection apparatus 200 is at the position of reference value S1 (for example, the position of a height of 97 cm shown in FIG. 2) of the height reached by bouncing indenter 2 at replacement time point is determined in FIG. 2 of the first embodiment. Height reference plate 12 is attached so as to be fixed to the top portions of struts 5, substantially overlaps base 4 as seen in plan view (overlaps particularly the position where indenter 2 is disposed as seen in plan view), and has a rectangular planar shape, for example.

In FIG. 7, however, in order to allow height reference plate 12 to be readily visually recognized as a member independent from base 4, height reference plate 12 is shown with a dotted line, and to have an edge slightly inside base 4.

Inspection apparatus 200 is different from inspection apparatus 100 only in that it has height reference plate 12 as described above, and is otherwise substantially the same in configuration as inspection apparatus 100. Hence, the same elements are designated by the same signs and the description thereof will not be repeated.

Figure 8:
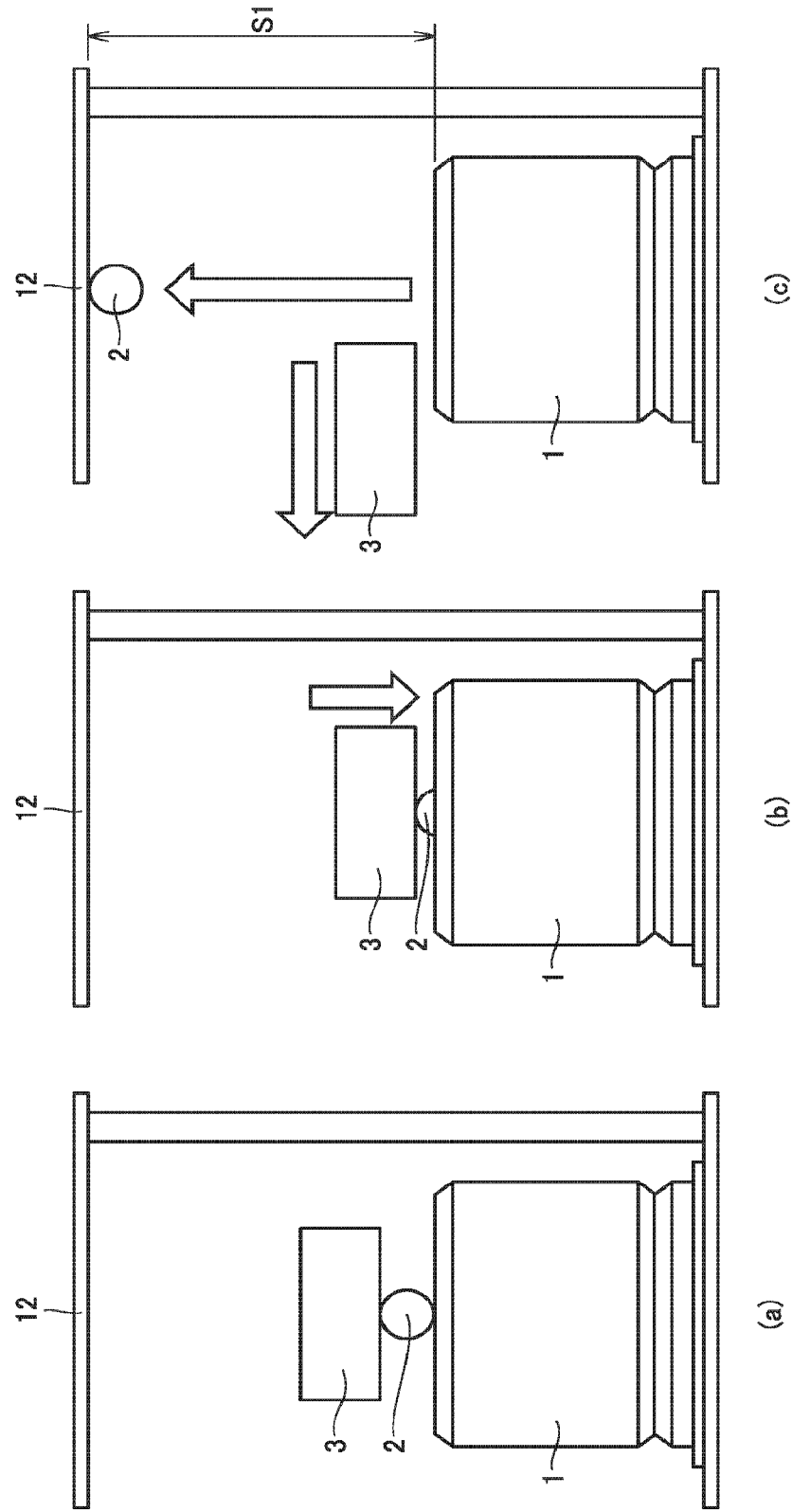
FIG. 8 is a schematic diagram (a) showing a step in a preparation stage for a step of pressing an indenter formed of a spherical object when the inspection apparatus according to the second embodiment is used; a schematic diagram (b) showing the step of pressing the indenter formed of a spherical object when the inspection apparatus according to the second embodiment is used; and a schematic diagram (c) showing a step of causing the indenter formed of a spherical object to bounce and detecting whether or not the indenter reaches a height reference plate when the inspection apparatus according to the second embodiment is used.

Referring to FIGS. 8(*a*), (*b*) and (*c*) illustrating an overview of an inspection method in this embodiment, these are basically the same as FIGS. 1(*a*), (*b*) and (*c*), respectively, illustrating the overview of the inspection method in the first embodiment. That is, FIG. 8(*a*) corresponds to the step of FIG. 1(*a*) in the first embodiment, FIG. 8(*b*) corresponds to the step of FIG. 1(*b*) in the first embodiment, and FIG. 8(*c*) corresponds to the step of FIG. 1(*c*) in the first embodiment.

Again, in this embodiment, in the step of FIG. 8(*c*), that is, the step of measuring the physical property value indicative of the repulsive force when the load of pressing indenter 2 into resin shock absorber 1 by load applying plate 3 is released, a height reached by indenter 2 experiencing the repulsive force and bouncing upward serves as the physical property value indicative of the repulsive force. In FIG. 8(*c*), however, instead of measuring the height reached by indenter 2 by means of height display plate 8 as in the first embodiment, it is detected whether or not indenter 2 reaches height reference plate 12.

That is, if indenter 2 reaches height reference plate 12, it means that indenter 2 rises to a height equal to or higher than that of height reference plate 12, and therefore, it can be determined that resin shock absorber 1 does not need to be replaced. In contrast, if indenter 2 does not reach height reference plate 12, it can be determined that resin shock absorber 1 needs to be replaced.

Figure 9:
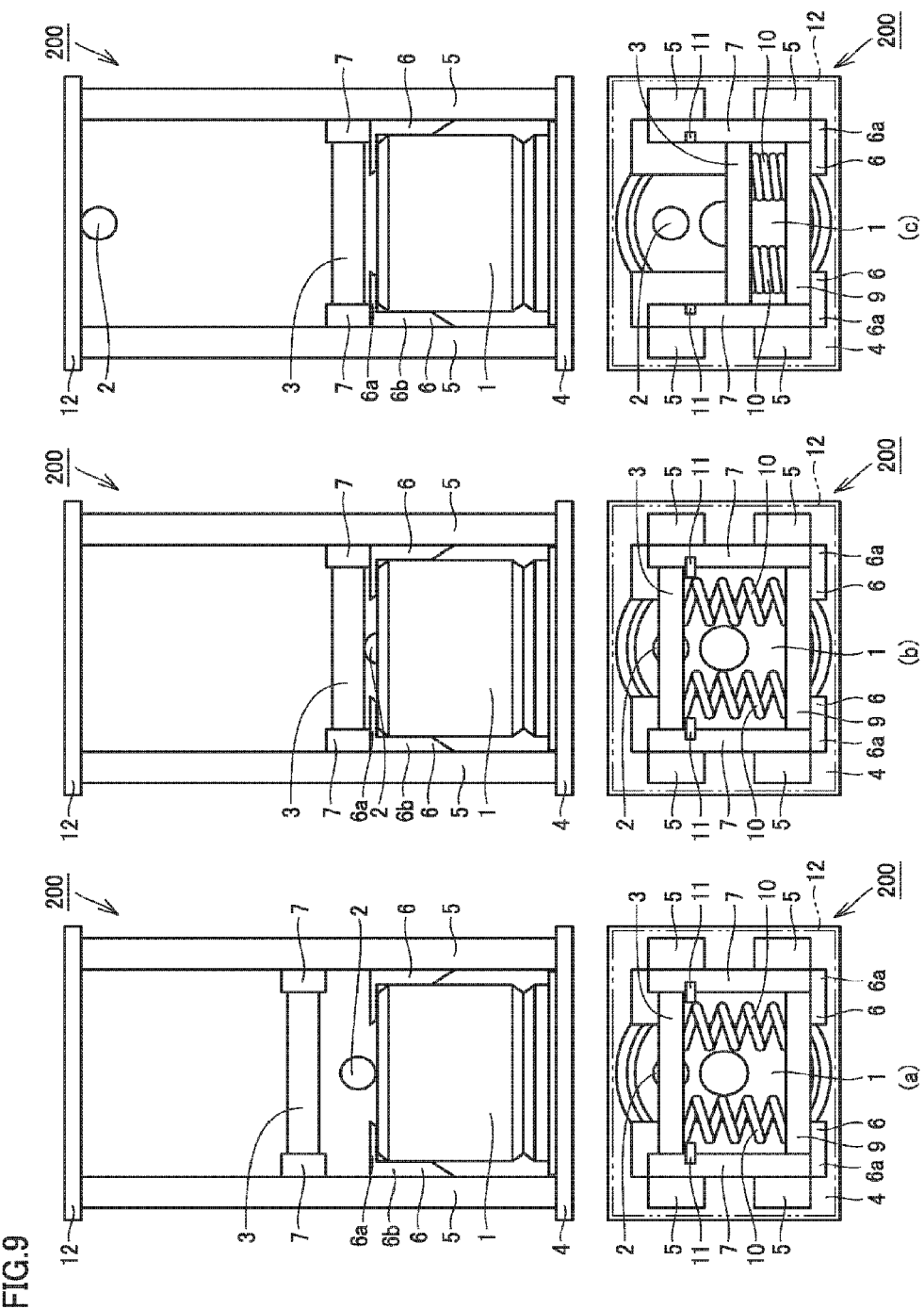
FIG. 9 is a schematic front view and a schematic plan view (a), corresponding to the state of FIG. 8(a), showing an aspect of each member in the preparation stage for the step of pressing the indenter formed of a spherical object when the inspection apparatus according to the second embodiment is used; a schematic front view and a schematic plan view (b), corresponding to the state of FIG. 8(b), showing an aspect of each member in the step of pressing the indenter formed of a spherical object when the inspection apparatus according to the second embodiment is used; and a schematic front view and a schematic plan view (c), corresponding to the state of FIG. 8(c), showing an aspect of each member in the step of causing the indenter formed of a spherical object to bounce and detecting whether or not the indenter reaches the height reference plate when the inspection apparatus according to the second embodiment is used.

Referring to FIGS. 9(*a*), (*b*) and (*c*), the operation of each member in the inspection step of resin shock absorber 1 using inspection apparatus 200 of FIGS. 6 and 7 is basically the same as the operation of each member in the inspection step using inspection apparatus 100 in the first embodiment shown in FIGS. 5(*a*), (*b*) and (*c*), respectively. FIG. 9(*c*) is different from FIG. 5(*c*) only in that, instead of determining the height reached by bouncing indenter 2 by means of height display plate 8, it is detected whether or not indenter 2 reaches height reference plate 12.

The inspection method of this embodiment is different from the first embodiment only in the above respect, and is otherwise the same as the first embodiment. Hence, the same elements are designated by the same signs and the description thereof will not be repeated.

The function and effect of this embodiment will now be described.

Again, in this embodiment, reference value S1 of the height reached by indenter 2 at replacement time point is of resin shock absorber 1 is determined from the data of FIG. 2, as in the first embodiment. By so doing, during inspections thereafter, the necessity of replacement of resin shock absorber 1 can be determined merely by providing inspection apparatus 200 with height reference plate 12 located at the height of reference value S1 and detecting whether or not indenter 2 reaches height reference plate 12. This can eliminate the need to make a measurement using an elevator car at an inspection location, thereby allowing the inspection to be simply performed, as in the first embodiment.

This inspection method is simple and improves the measurement accuracy as compared to the method of measuring the bounce height of indenter 2 by means of height display plate 8 in the first embodiment. That is, in the method using height display plate 8 of the first embodiment, for example, when visually checking the bounce height of indenter 2, failed or erroneous checking may result. When checking the bounce height of indenter 2 from video recording, it takes time and effort to set up the recording device and the like. In this embodiment, however, it is only required to detect whether or not indenter 2 reaches height reference plate 12, thereby reducing the possibility of the occurrence of a human error as mentioned above, and also reducing the time and effort for the preparation for the measurement and the like.

Third Embodiment

Figure 10:
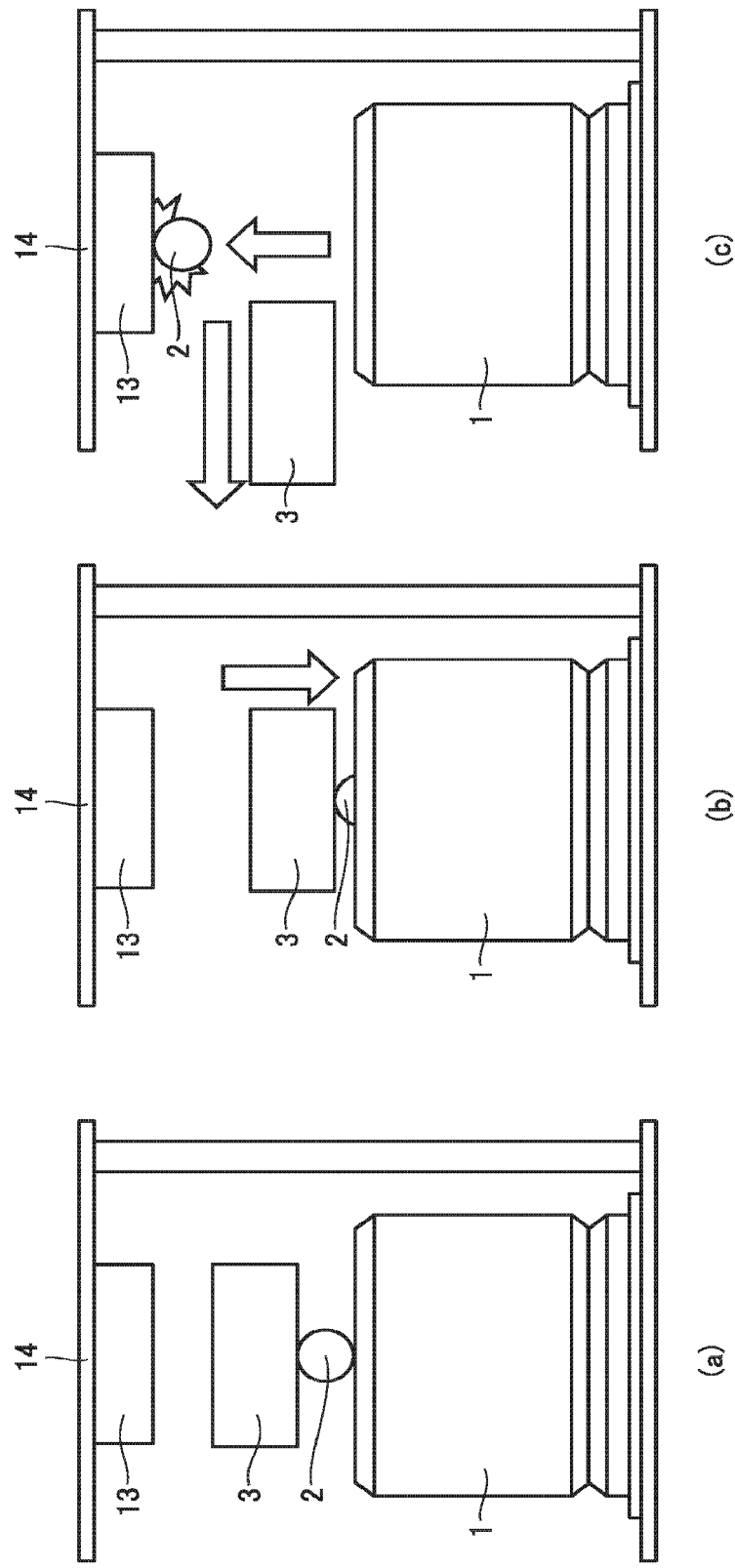
FIG. 10 is a schematic diagram (a) showing a step in a preparation stage for a step of pressing an indenter formed of a spherical object when an inspection apparatus according to a third embodiment is used; a schematic diagram (b) showing the step of pressing the indenter formed of a spherical object when the inspection apparatus according to the third embodiment is used; and a schematic diagram (c) showing a step of causing the indenter formed of a spherical object to bounce and measuring a collision load thereof when the inspection apparatus according to the third embodiment is used.

Referring to FIGS. 10(*a*), (*b*) and (*c*) illustrating an overview of an inspection method in this embodiment, these are basically the same as FIGS. 1(*a*), (*b*) and (*c*), respectively, illustrating the overview of the inspection method in the first embodiment.

In this embodiment, however, in the step of FIG. 10(*c*), that is, the step of measuring the physical property value indicative of the repulsive force when the load of pressing indenter 2 into resin shock absorber 1 by load applying plate 3 is released, a load when indenter 2 collides with a load detector 13 (load detection device) is measured as the physical property value. The load upon collision as used herein means a force exerted on load detector 13 by indenter 2 in the vertical direction (directly upward direction). In this manner, this embodiment is different in the method of measuring the physical property value indicative of the repulsive force experienced by indenter 2, from the first embodiment in which the height reached by indenter 2 is measured by means of height display plate 8.

Load detector 13 is installed, for example, on a surface of a ceiling portion 14 fixed to the top portions of struts 5, on the side facing resin shock absorber 1 and the like (lower side). Load detector 13 is provided substantially directly above the position where indenter 2 is placed, particularly on a trajectory of the bounce of indenter 2.

Load detector 13 is provided, regarding the height from resin shock absorber 1, at a position lower than height reference plate 12 in the second embodiment, for example. That is, in order to be able to receive the collision of indenter 2 even when the height reached by indenter 2 is lower than reference value S1 of the bounce height described above (see FIG. 2), load detector 13 is provided at a position lower than height reference plate 12 of the second embodiment based on the premise that load detector 13 will also collide with indenter 2 basically having a small bouncing force.

In this embodiment, a result of the load due to the collision of indenter 2 measured by load detector 13 (collision load) is compared with a reference value prepared in advance. As a result, if the result exceeds the reference value, it is determined that resin shock absorber 1 has a high elastic force and a high force of cushioning the impact force due to the collision of a car, and it is thus determined that resin shock absorber 1 does not need to be replaced. In contrast, if the result falls below the reference value, it is determined that resin shock absorber 1 has a low elastic force and a low force of cushioning the impact force due to the collision of a car, and it is thus determined that resin shock absorber 1 needs to be replaced. The magnitude of the collision load is basically correlated with the magnitude of the bounce height of the first embodiment.

A method of determining the reference value of the collision load of indenter 2 at which resin shock absorber 1 needs to be replaced in this embodiment is basically the same as the method of determining the reference value of the bounce height of indenter 2 in the first embodiment, and will be described with reference to FIG. 11.

Referring to FIG. 11(a), this graph is basically the same as the graph of FIG. 2(a) in the first embodiment, where the average deceleration upon collision of the car, which was measured while each period of use of resin shock absorber 1 (or the period regarded as a period of use by an accelerated deterioration test) was varied, is plotted as a dot A1 to a dot A6.

Referring to FIG. 11(b), resin shock absorber 1 that has been subjected to the measurement of the average deceleration of the car is subjected, at the same time as each of the measurements of dot A1 to dot A6, to a step of pressing indenter 2 into resin shock absorber 1 and releasing indenter 2 in the manner shown in FIG. 10, and causing indenter 2 bouncing upon the release to collide with load detector 13 to measure the collision load by load detector 13. Each of these results is plotted as a dot C1 to a dot C6 in FIG. 11(b). By connecting dot C1 to dot C6, a curve is obtained that indicates relation between the period of use of resin shock absorber 1 (the period regarded as a period of use by an accelerated deterioration test) and the collision load of indenter 2 with respect to load detector 13.

Referring to FIGS. 11(a) and 11(c), a collision load S2 of indenter 2 at replacement time point ts when the average deceleration of the car reaches 9.8 m/s$^2$ is determined as the reference value to replace resin shock absorber 1. In FIG. 11(c), collision load S2 of indenter 2 serving as the reference value to replace resin shock absorber 1 is about 19 N.

As in FIG. 2, it can be determined that resin shock absorber 1 does not need to be replaced at each time point of point A1 to point A4 and point C1 to point C4 with a shorter period of use than replacement time point ts, and that resin shock absorber 1 needs to be replaced at each time point of points A5, A6 and points B5, B6 with a longer period of use than replacement time point ts.

The above collision load of indenter 2 with respect to load detector 13 varies with the height at which load detector 13 is installed from the top surface of resin shock absorber 1. Thus, it is required that the aforementioned parameter (the height at which load detector 13 is installed from the top surface of resin shock absorber 1) have a constant value when obtaining the plot data of point C1 to point C6 in FIGS. 11(b) and (c) described above, and thereafter when measuring the collision load of indenter 2 with respect to load detector 13 for resin shock absorber 1 at an elevator inspection location.

As load detector 13 is installed at a lower position from the top surface of resin shock absorber 1, a higher collision load is applied to load detector 13 by bouncing indenter 2, thus allowing for more accurate determination of the necessity of replacement of resin shock absorber 1. The height of load detector 13 in the vertical direction from the top surface of resin shock absorber 1 is preferably equal to or more than 50 cm and equal to or less than 80 cm, for example, and more preferably equal to or more than 50 cm and equal to or less than 70 cm. By way of example, in this embodiment, it is preferable that the height of load detector 13 in the vertical direction from the top surface of resin shock absorber 1 be set at 70 cm.

Figure 12:
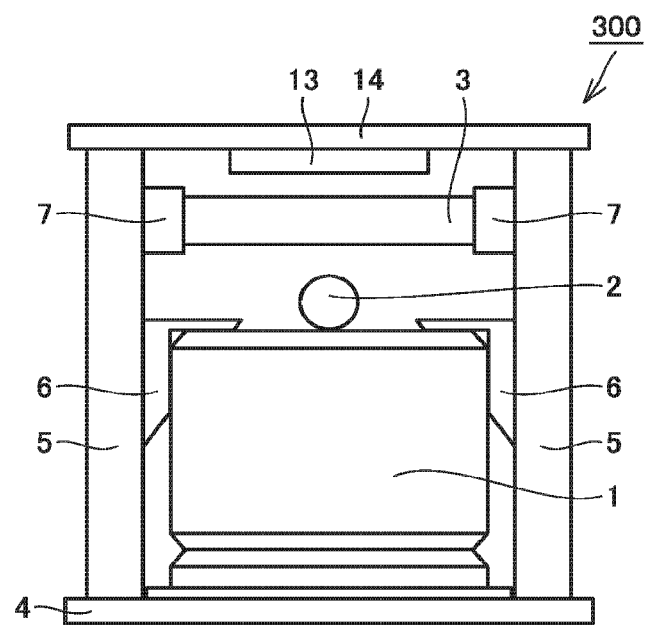
FIG. 12 is a schematic front view showing the configuration of the inspection apparatus according to the third embodiment.
Figure 13:
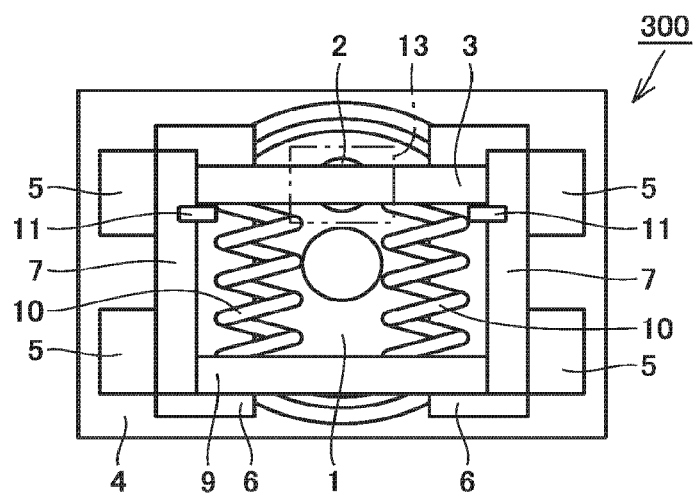
FIG. 13 is a schematic plan view showing the configuration of the inspection apparatus according to the third embodiment.

Referring to FIGS. 12 and 13, an inspection apparatus 300 of this embodiment basically has the same configuration as that of inspection apparatus 100 of the first embodiment, but is different from inspection apparatus 100 in that it has load detector 13 as the measuring mechanism above load applying plate 3. In FIG. 13, however, in order to allow the other members included in inspection apparatus 300 to be visually recognized, the load detector is shown with a dotted line.

Figure 14:
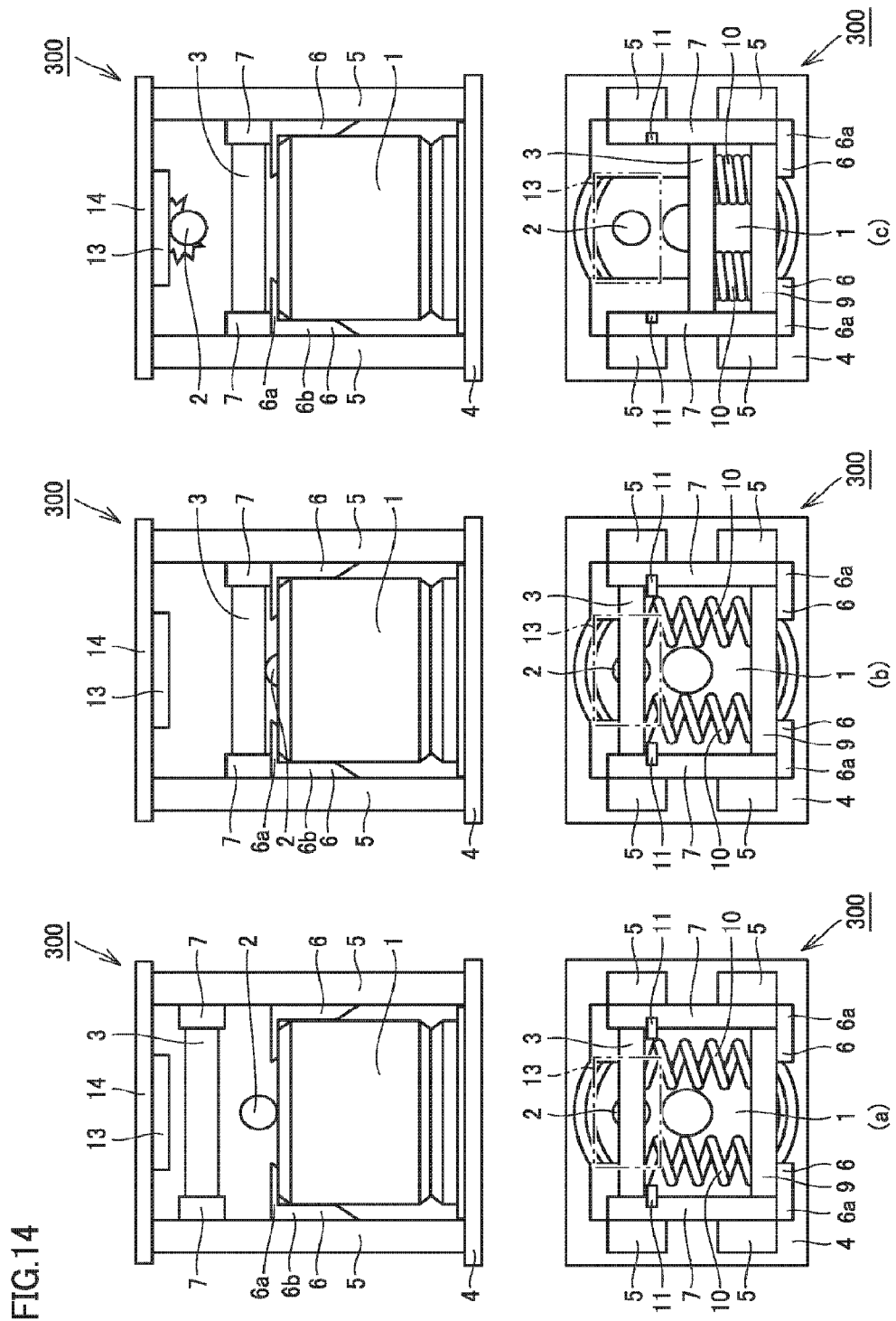
FIG. 14 is a schematic front view and a schematic plan view (a), corresponding to the state of FIG. 10(a), showing an aspect of each member in the preparation stage for the step of pressing the indenter formed of a spherical object when the inspection apparatus according to the third embodiment is used; a schematic front view and a schematic plan view (b), corresponding to the state of FIG. 10(b), showing an aspect of each member in the step of pressing the indenter formed of a spherical object when the inspection apparatus according to the third embodiment is used; and a schematic front view and a schematic plan view (c), corresponding to the state of FIG. 10(c), showing an aspect of each member in the step of causing the indenter formed of a spherical object to bounce and measuring the collision load when the inspection apparatus according to the third embodiment is used.

Referring to FIGS. 14(a), (b) and (c), the operation of each member in the inspection step of resin shock absorber 1 using inspection apparatus 300 of FIGS. 12 and 13 is basically the same as the operation of each member in the inspection step using inspection apparatus 100 in the first embodiment shown in FIGS. 5(a), (b) and (c), respectively. FIG. 14(c) is different from FIG. 5(c) only in that, instead of determining the height reached by bouncing indenter 2 by means of height display plate 8, the collision load is detected by load detector 13.

Inspection apparatus 300 is different from inspection apparatus 100 only in that it has load detector 13 as described above, and is otherwise substantially the same in configuration as inspection apparatus 100. Hence, the same elements are designated by the same signs and the description thereof will not be repeated.

The function and effect of this embodiment will now be described.

Replacement time point is indicative of the time when the replacement is needed varies, even among resin shock absorbers 1 of the same model number, with the installation environment such as temperature and humidity. However, at least that the average deceleration is 9.8 m/s$^2$ and the collision load when indenter 2 bounces is 19 N at replacement time point is remains substantially the same among resin shock absorbers 1 of the same model number, regardless of the installation environment such as temperature and humidity.

Figure 11:
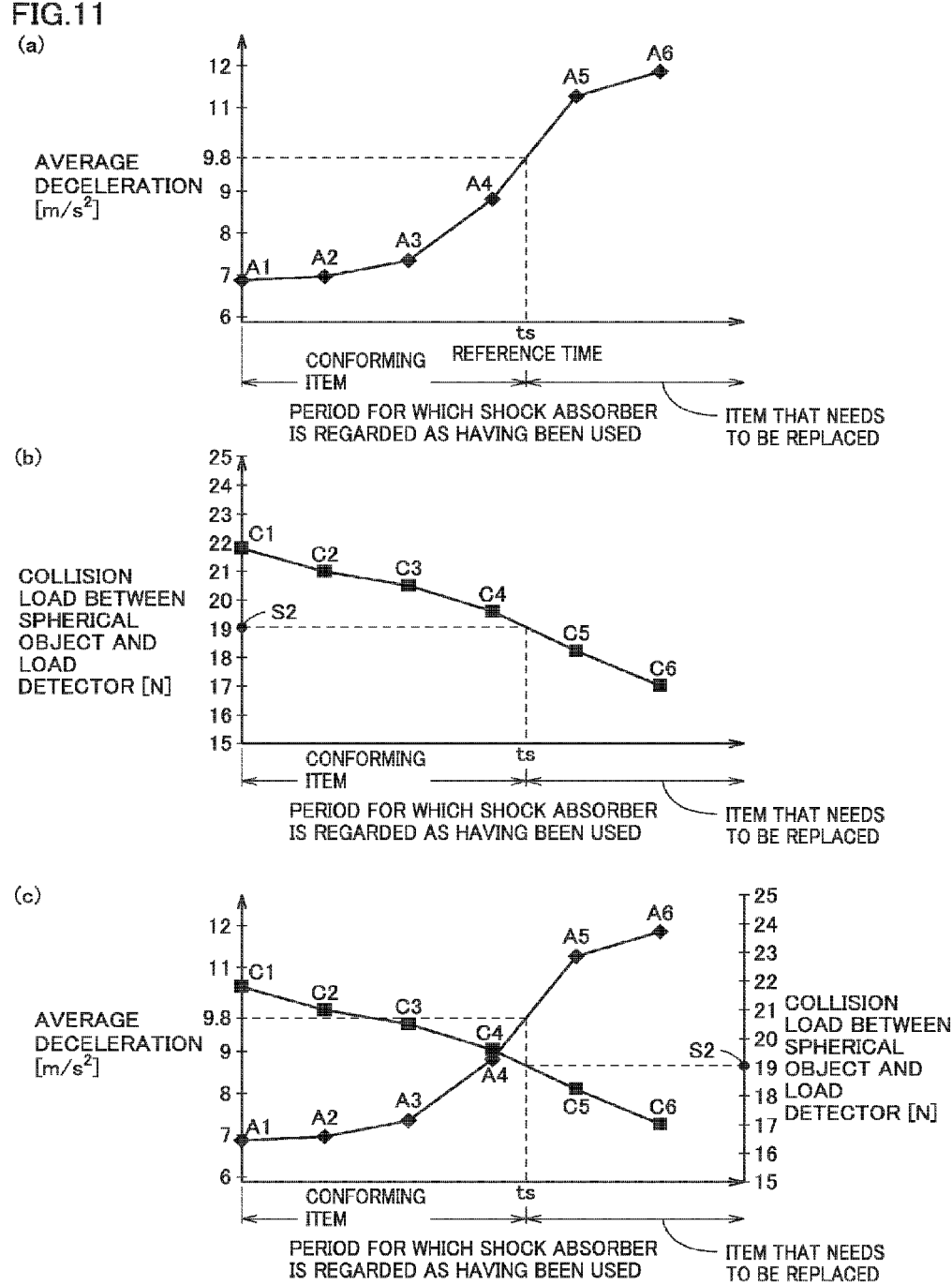
FIG. 11 is a graph (a) showing relation between a period of use of a resin shock absorber and an average deceleration of a car colliding with the resin shock absorber in the third embodiment; a graph (b) showing relation between the period of use of the resin shock absorber and the collision load of the indenter formed of a spherical object bouncing from the resin shock absorber in the third embodiment; and a graph (c) combining the above FIGS. 11(a) and 11(b) together.

Accordingly, in this embodiment, once a reference value S2 of the collision load of indenter 2 with respect to load detector 13 is determined from the data of FIG. 11, during inspections thereafter, the necessity of replacement of resin shock absorber 1 can be determined merely by detecting whether the collision load of indenter 2 bouncing from resin shock absorber 1 is equal to or greater than reference value S2, or less than reference value S2. This can eliminate the need to make a measurement using an elevator car at an inspection location, thereby allowing the inspection to be simply performed, as in the first embodiment.

Furthermore, in this embodiment, load detector 13 is installed at a relatively low position from resin shock absorber 1. Accordingly, inspection apparatus 300 of this embodiment has a smaller dimension in the height direction of the apparatus body than inspection apparatuses 100, 200 employing height display plate 8 of the first embodiment or height reference plate 12 of the second embodiment, for example, thereby having a smaller size of the apparatus body.

Moreover, in this embodiment, the possibility of the occurrence of a human error in a measurement result can be reduced as compared to the example where the measurement is visually made by means of height display plate 8 as in the first embodiment, for example.

Fourth Embodiment

Referring to FIGS. 15(a), (b) and (c) illustrating an overview of an inspection method in this embodiment, these are basically the same as FIGS. 1(a), (b) and (c), respectively, illustrating the overview of the inspection method in the first embodiment.

In this embodiment, however, in the step of FIG. 15(c), that is, the step of measuring the physical property value indicative of the repulsive force when the load of pressing indenter 2 into resin shock absorber 1 by load applying plate 3 is released, a speed of indenter 2 bouncing upward from resin shock absorber 1 is measured by a speed measurement device 15 as the physical property value. The speed as used herein means a speed in the vertical direction (directly upward direction). In this manner, this embodiment is different from the first embodiment in the method of measuring the physical property value indicative of the repulsive force experienced by indenter 2.

Speed measurement device 15 is fixed to the side of strut 5 facing resin shock absorber 1 (inner side of the apparatus body), and measures the speed of indenter 2 when indenter 2 passes upward through a portion of the trajectory of the bounce of indenter 2.

Speed measurement device 15 is provided, regarding the height from resin shock absorber 1, at a position lower than height reference plate 12 in the second embodiment, for example. That is, in order to be able to detect the passage of indenter 2 moving upward and measure the speed thereof even when the height reached by indenter 2 is lower than reference value S1 of the bounce height described above (see FIG. 2), speed measurement device 15 is provided at a position lower than height reference plate 12 of the second embodiment based on the premise that speed measurement device 15 will also detect the speed of indenter 2 basically having a small bouncing force. As shown in each drawing of FIG. 15, speed measurement device 15 is basically a member extending in the horizontal direction, and is configured so as to be able to detect the speed of indenter 2 passing through a height substantially equal to the height at which speed measurement device 15 is installed in the vertical direction.

In this embodiment, a result of the speed of indenter 2 measured by speed measurement device 15 is compared with a reference value prepared in advance. As a result, if the result exceeds the reference value, it is determined that resin shock absorber 1 has a high elastic force and a high force of cushioning the impact force due to the collision of a car, and it is thus determined that resin shock absorber 1 does not need to be replaced. In contrast, if the result falls below the reference value, it is determined that resin shock absorber 1 has a low elastic force and a low force of cushioning the impact force due to the collision of a car, and it is thus determined that resin shock absorber 1 needs to be replaced. The magnitude of the speed is basically correlated with the magnitude of the bounce height in the first embodiment.

A method of determining the reference value of the speed of indenter 2 at which resin shock absorber 1 needs to be replaced in this embodiment is basically the same as the method of determining the reference value of the bounce height of indenter 2 in the first embodiment, and will be described with reference to FIG. 16.

Referring to FIG. 16(a), this graph is basically the same as the graph of FIG. 2(a) in the first embodiment, where the average deceleration upon collision of the car, which was measured while each period of use of resin shock absorber 1 (or the period regarded as a period of use by an accelerated deterioration test) was varied, is plotted as a dot A1 to a dot A6.

Figure 15:
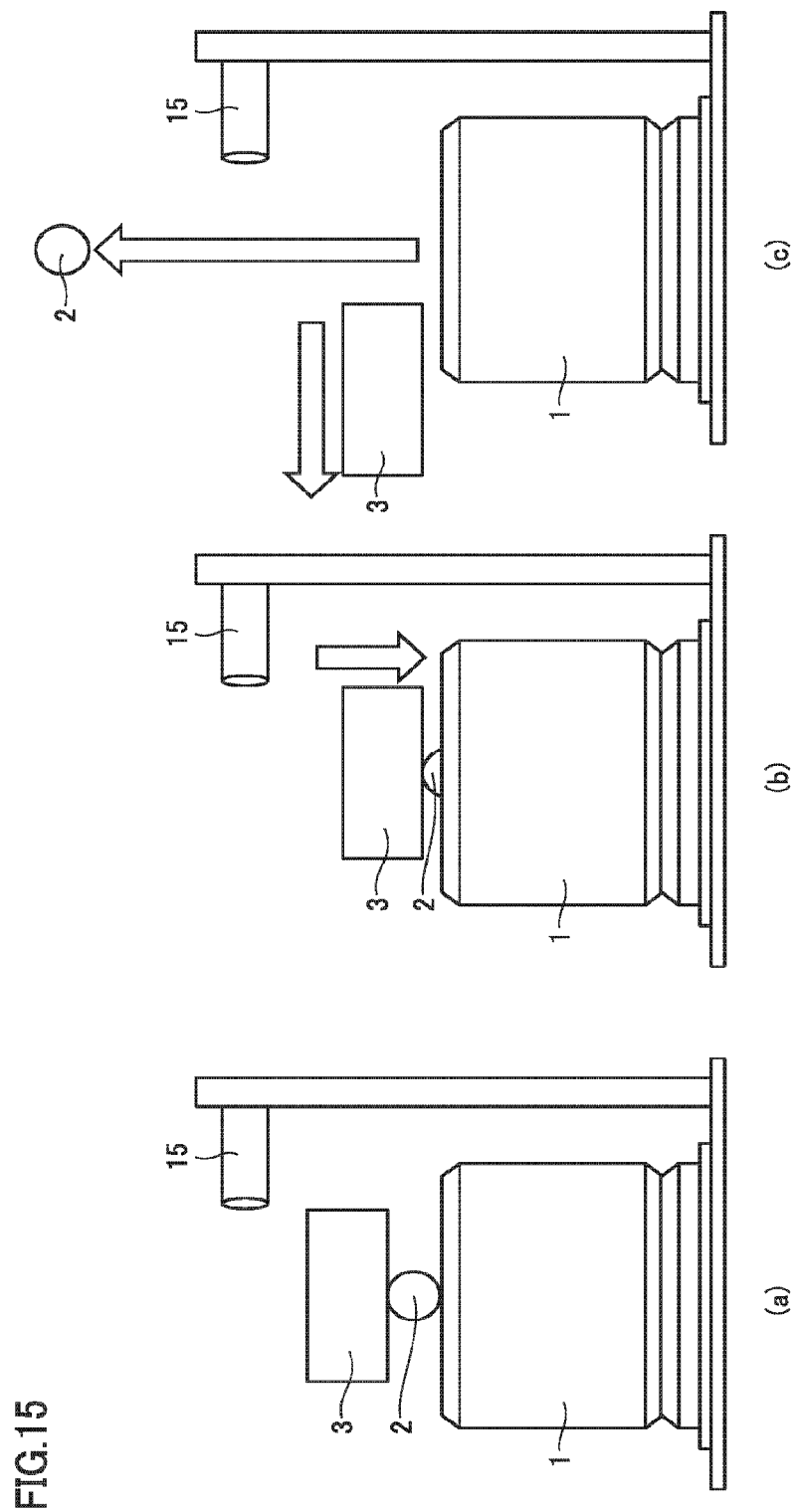
FIG. 15 is a schematic diagram (a) showing a step in a preparation stage for a step of pressing an indenter formed of a spherical object when an inspection apparatus according to a fourth embodiment is used; a schematic diagram (b) showing the step of pressing the indenter formed of a spherical object when the inspection apparatus according to the fourth embodiment is used; and a schematic diagram (c) showing a step of causing the indenter formed of a spherical object to bounce and measuring a speed thereof when the inspection apparatus according to the fourth embodiment is used.

Referring to FIG. 16(b), resin shock absorber 1 that has been subjected to the measurement of the average deceleration of the car is subjected, at the same time as each of the measurements of dot A1 to dot A6, to a step of pressing indenter 2 into resin shock absorber 1 and releasing indenter 2 in the manner shown in FIG. 15, and measuring the speed of indenter 2 bouncing upon the release by speed measurement device 15. Each of these results is plotted as a dot D1 to a dot D6 in FIG. 16(b). By connecting dot D1 to dot D6, a curve is obtained that indicates relation between the period of use of resin shock absorber 1 (the period regarded as a period of use by an accelerated deterioration test) and the measured speed of indenter 2.

Referring to FIGS. 16(a) and 16(c), the bounce speed of indenter 2 at replacement time point ts when the average deceleration of the car reaches 9.8 m/s$^2$ is determined as the reference value to replace resin shock absorber 1. In FIG. 16(c), a speed S3 of indenter 2 serving as the reference value to replace resin shock absorber 1 is about 40 km/h.

As in FIG. 2, it can be determined that resin shock absorber 1 does not need to be replaced at each time point of point A1 to point A4 and point D1 to point D4 with a shorter period of use than replacement time point ts, and that resin shock absorber 1 needs to be replaced at each time point of points A5, A6 and points D5, D6 with a longer period of use than replacement time point ts.

The above speed of indenter 2 measured by speed measurement device 15 varies with the height at which speed measurement device 15 is installed from the top surface of resin shock absorber 1. Thus, it is required that the aforementioned parameter (the height at which speed measurement device 15 is installed from the top surface of resin shock absorber 1) have a constant value when obtaining the plot data of point D1 to point D6 in FIGS. 16(b) and (c) described above, and thereafter when measuring the speed of indenter 2 for resin shock absorber 1 at an elevator inspection location.

As speed measurement device 15 is installed at a lower position from the top surface of resin shock absorber 1, a higher speed of bouncing indenter 2 is measured by speed measurement device 15, thus allowing for more accurate determination of the necessity of replacement of resin shock absorber 1. The height of speed measurement device 15 in the vertical direction from the top surface of resin shock absorber 1 is preferably equal to or more than 50 cm and equal to or less than 80 cm, for example, and more preferably equal to or more than 50 cm and equal to or less than 70 cm. By way of example, in this embodiment, it is preferable that the height of speed measurement device 15 in the vertical direction from the top surface of resin shock absorber 1 be set at 70 cm.

Figure 17:
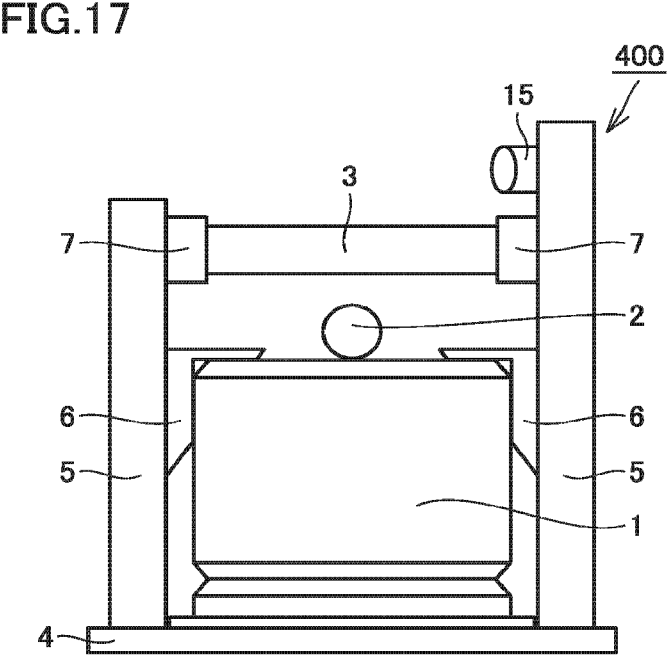
FIG. 17 is a schematic front view showing the configuration of the inspection apparatus according to the fourth embodiment.
Figure 18:
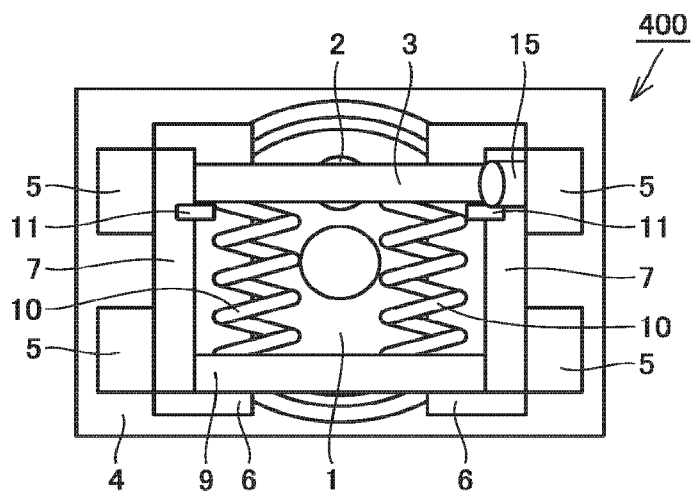
FIG. 18 is a schematic plan view showing the configuration of the inspection apparatus according to the fourth embodiment.

Referring to FIGS. 17 and 18, an inspection apparatus 400 of this embodiment basically has the same configuration as that of inspection apparatus 100 of the first embodiment, but is different from inspection apparatus 100 in that it has speed measurement device 15 as the measuring mechanism above load applying plate 3. It is preferable for speed measurement device 15 to be installed at a position substantially the same as the position to which indenter 2 bounces with respect to the depth direction of the apparatus body (the up-down direction in FIG. 18), and a position at a distance from the position to which indenter 2 bounces with respect to the width direction of the apparatus body (the right-left direction in FIG. 18) (for example, a position to the right of indenter 2).

Figure 19:
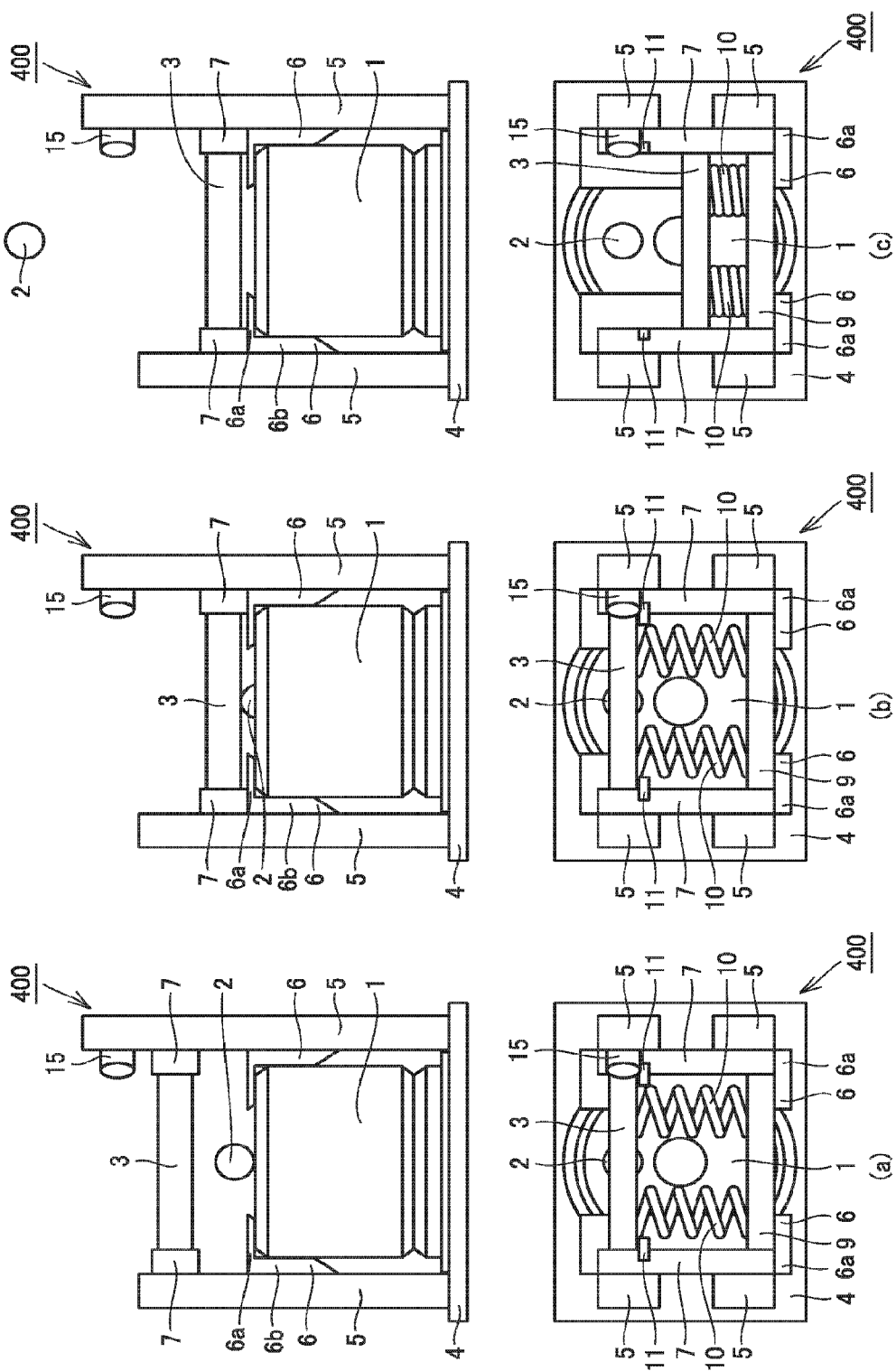
FIG. 19 is a schematic front view and a schematic plan view (a), corresponding to the state of FIG. 15(a), showing an aspect of each member in the preparation stage for the step of pressing the indenter formed of a spherical object when the inspection apparatus according to the fourth embodiment is used; a schematic front view and a schematic plan view (b), corresponding to the state of FIG. 15(b), showing an aspect of each member in the step of pressing the indenter formed of a spherical object when the inspection apparatus according to the fourth embodiment is used; and a schematic front view and a schematic plan view (c), corresponding to the state of FIG. 15(c), showing an aspect of each member in the step of causing the indenter formed of a spherical object to bounce and measuring the speed thereof when the inspection apparatus according to the fourth embodiment is used.

Referring to FIGS. 19(a), (b) and (c), the operation of each member in the inspection step of resin shock absorber 1 using inspection apparatus 400 of FIGS. 17 and 18 is basically the same as the operation of each member in the inspection step using inspection apparatus 100 in the first embodiment shown in FIGS. 5(a), (b) and (c), respectively. FIG. 19(c) is different from FIG. 5(c) only in that, instead of determining the height reached by bouncing indenter 2 by means of height display plate 8, the speed of indenter 2 is measured by speed measurement device 15.

Inspection apparatus 400 is different from inspection apparatus 100 only in that it has speed measurement device 15 as described above, and is otherwise substantially the same in configuration as inspection apparatus 100. Hence, the same elements are designated by the same signs and the description thereof will not be repeated.

The function and effect of this embodiment will now be described.

Replacement time point ts indicative of the time when the replacement is needed varies, even among resin shock absorbers 1 of the same model number, with the installation environment such as temperature and humidity. However, at least that the average deceleration is 9.8 m/s$^2$ and the speed of indenter 2 is 40 km/h at replacement time point ts remains substantially the same among resin shock absorbers 1 of the same model number, regardless of the installation environment such as temperature and humidity.

Accordingly, in this embodiment, once a reference value S3 of the bounce speed of indenter 2 is determined from the data of FIG. 16, during inspections thereafter, the necessity of replacement of resin shock absorber 1 can be determined merely by detecting whether the speed of indenter 2 bouncing from resin shock absorber 1 is equal to or greater than reference value S3 or less than reference value S3. This can eliminate the need to make a measurement using an elevator car at an inspection location, thereby allowing the inspection to be simply performed, as in the first embodiment.

Furthermore, in this embodiment, speed measurement device 15 is installed at a relatively low position from resin shock absorber 1. Accordingly, inspection apparatus 400 of this embodiment has a smaller dimension in the height direction of the apparatus body than inspection apparatuses 100, 200 employing height display plate 8 of the first embodiment or height reference plate 12 of the second embodiment, for example, thereby having a smaller size of the apparatus body.

Moreover, in this embodiment, the possibility of the occurrence of a human error in a measurement result can be reduced as compared to the example where the measurement is visually made by means of height display plate 8 as in the first embodiment, for example.

Fifth Embodiment

In this embodiment, an inspection is basically made with the same inspection methods of the first to fourth embodiments, but the shape of indenter 2 is different from that of the first to fourth embodiments. Accordingly, the configuration of the inspection apparatus is also slightly different from those of the first to fourth embodiments.

It is preferable that indenter 2 of this embodiment have such hardness that it deforms to a negligible extent when pressed into resin shock absorber 1, and have such a shape that does not damage the surface of resin shock absorber 1 when pressed into resin shock absorber 1.

Figure 20:
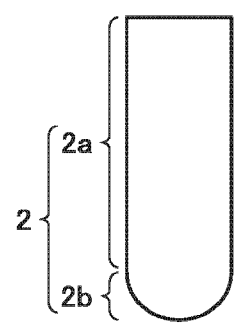
FIG. 20 is a schematic diagram showing the shape of an indenter extending in a rod-like manner, for use in an inspection apparatus according to a fifth embodiment.
Figure 24:
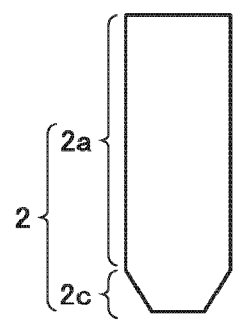
FIG. 24 is a schematic diagram showing a variation of the shape of the indenter, for use in the inspection apparatus according to the fifth embodiment.

Specifically, referring to FIG. 20, indenter 2 used in this embodiment is made of metal such as stainless steel or iron as in the first embodiment, but has the shape of an extending rod. That is, indenter 2 has a rod-like portion 2a extending in a rod-like manner, and a spherical portion 2b formed at the side of one end portion with respect to a direction in which rod-like portion 2a extends. The side of the pair of end portions of indenter 2 at which spherical portion 2b is formed is the side that will make contact with resin shock absorber 1. Referring to FIG. 24, however, indenter 2 may have, for example, rod-like portion 2a extending in a rod-like manner, and a polyhedron shape portion 2c formed at the side of the one end portion with respect to the direction in which rod-like portion 2a extends (in this case, the side at which polyhedron shape portion 2c is formed is the side that will make contact with resin shock absorber 1).

It is noted that rod-like portion 2a may have a columnar shape or rectangular column shape (for example, square column shape), but more preferably has a columnar shape (particularly when indenter 2 has spherical portion 2b or polyhedron shape portion 2c). In addition, although not illustrated, indenter 2 may have a columnar shape or rectangular column shape having only rod-like portion 2a as a whole.

Referring now to FIGS. 21(a), (b) and (c) illustrating an overview of an inspection method in this embodiment, these are basically the same as FIGS. 1(a), (b) and (c), respectively, illustrating the overview of the inspection method in the first embodiment.

This embodiment, however, is different in configuration from inspection apparatuses 100 to 400 of the other embodiments described above in that an inspection apparatus 500 has an indenter pressing jig 16 as the load applying mechanism. Indenter pressing jig 16 is disposed above and at a distance from resin shock absorber 1, and can move up and down as indicated by a downward arrow in FIG. 21(b) and an upward arrow in FIG. 21(c). Indenter pressing jig 16 includes stoppers 11, load applying plate 3 (not shown in FIG. 21) and the like.

Basically, FIG. 21(a) corresponds to the step of FIG. 1(a) and FIG. 5(a) in the first embodiment, for example, FIG. 21(b) corresponds to the step of FIG. 1(b) and FIG. 5(b) in the first embodiment, for example, and FIG. 21(c) corresponds to the step of FIG. 1(c) and FIG. 5(c) in the first embodiment, for example.

That is, in FIG. 21(a), load applying plate 3 is fixed by stopper 11 so as to be positioned above indenter 2. Indenter 2 is placed on the top surface of resin shock absorber 1. That is, FIG. 21(a) is a preparation stage for the step of pressing indenter 2 into resin shock absorber 1.

In FIG. 21(b), indenter pressing jig 16 descends, causing load applying plate 3 included therein to move downward so as to press indenter 2 downward. Indenter 2 (particularly spherical portion 2b or polyhedron shape portion 2c thereof) is thus pressed into resin shock absorber 1.

In FIG. 21(c), stopper 11 is removed, causing load applying plate 3 that has been constrained by stopper 11 to move to the right of the figure, for example, which causes the load of pressing indenter 2 into resin shock absorber 1 to be released. At this time, indenter 2 is subjected to a repulsive force from resin shock absorber 1 and bounces upward as indicated by an upward arrow in the figure. A height from resin shock absorber 1 that is reached by indenter 2 by this bounce is measured as the physical property value indicative of the repulsive force experienced by indenter 2.

Figure 21:
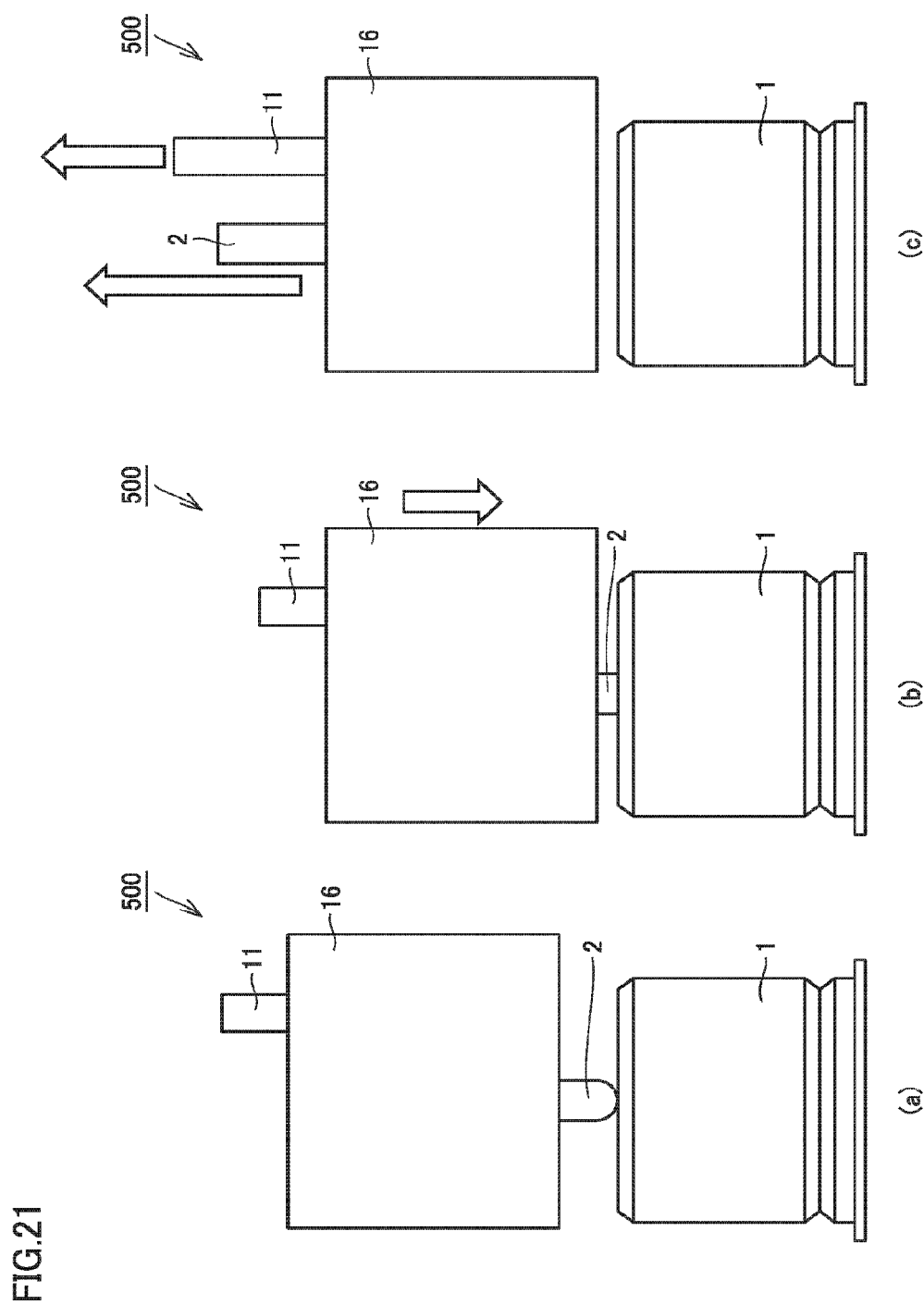
FIG. 21 is a schematic diagram (a) showing a step in a preparation stage for a step of pressing the indenter having the shape of an extending rod when the inspection apparatus according to the fifth embodiment is used; a schematic diagram (b) showing the step of pressing the indenter having the shape of an extending rod when the inspection apparatus according to the fifth embodiment is used; and a schematic diagram (c) showing a step of causing the indenter having the shape of an extending rod to bounce and measuring a collision load thereof when the inspection apparatus according to the fifth embodiment is used.
Figure 22:
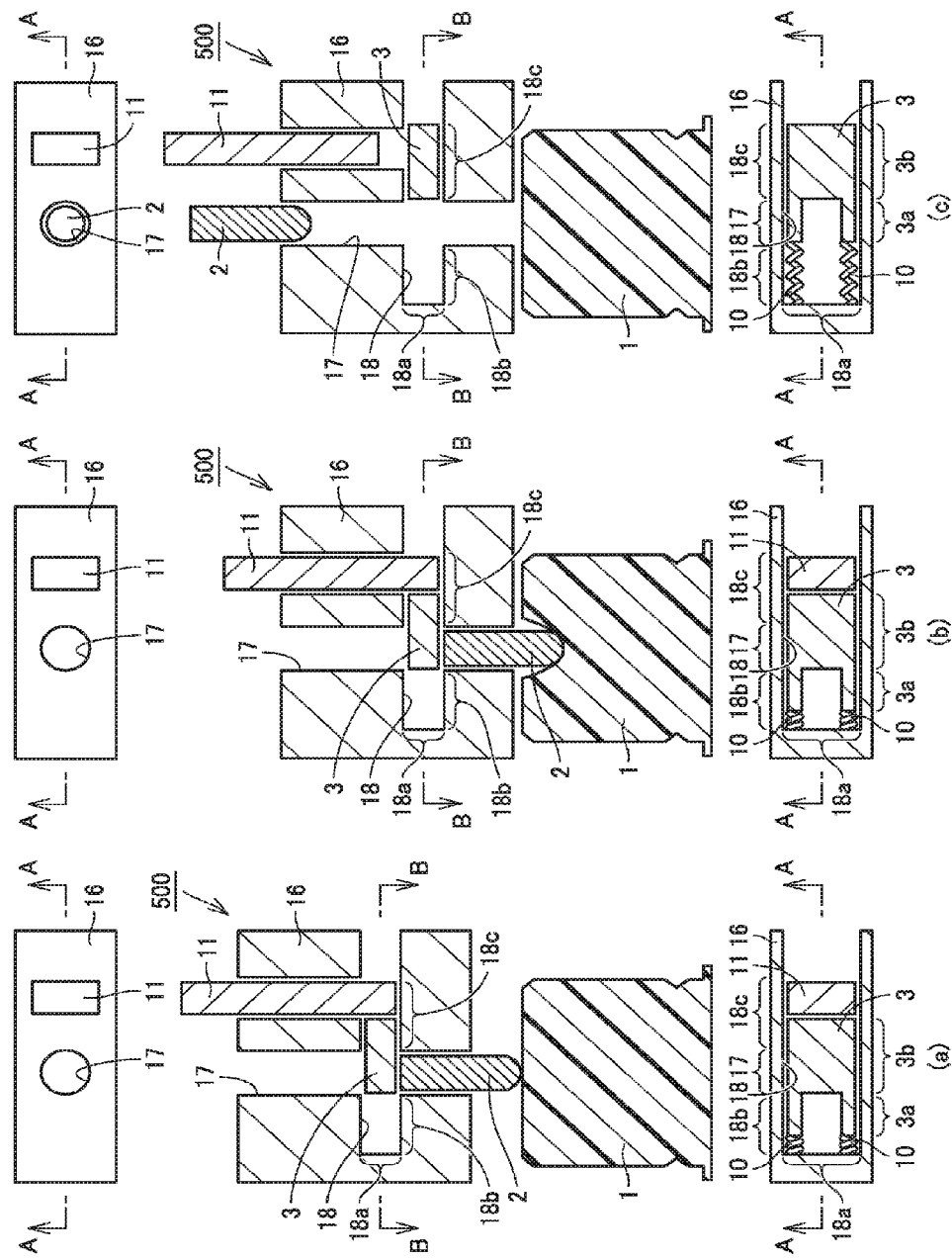
FIG. 22 is a schematic plan view and a schematic sectional view (a), corresponding to the state of FIG. 21(a), showing an aspect of the inside in a frontal direction and a planar direction of each member in the preparation stage for the step of pressing the indenter having the shape of an extending rod when the inspection apparatus according to the fifth embodiment is used; a schematic plan view and a schematic sectional view (b), corresponding to the state of FIG. 21(b), showing an aspect of the inside in the frontal direction and the planar direction of each member in the step of pressing the indenter having the shape of an extending rod when the inspection apparatus according to the fifth embodiment is used; and a schematic plan view and a schematic sectional view (c), corresponding to the state of FIG. 21(c), showing an aspect of the inside in the frontal direction and the planar direction of each member in the step of causing the indenter having the shape of an extending rod to bounce and measuring the collision load when the inspection apparatus according to the fifth embodiment is used.

Referring now to FIGS. 22(a), (b) and (c) showing an aspect of the inside of indenter pressing jig 16, the operation of each member in the inspection step of resin shock absorber 1 using inspection apparatus 500 of FIG. 21 is described in more detail.

Referring to FIG. 22(a), the top of three vertically aligned figures is a schematic plan view of particularly the portion of indenter pressing jig 16 of inspection apparatus 500, and the middle figure is a schematic sectional view of a portion along the line A-A in the top and bottom figures. The bottom figure is a schematic sectional view of a portion along the line B-B in the middle figure. In the middle figure, in order to facilitate understanding of the positional relation, resin shock absorber 1 disposed below indenter pressing jig 16 is also illustrated (the same being applied to FIGS. 22(b) and (c) to be described later).

Indenter pressing jig 16 has a hole portion for bouncing indenter 17 and a hole portion for sliding load applying plate 18 therein. Hole portion for bouncing indenter 17 is formed with an inner wall extending along the direction in which indenter 2 bounces (the up-down direction in the figure, that is, the vertical direction), and extends through the body of indenter pressing jig 16 in the up-down direction. It is preferable that the inner wall of hole portion for bouncing indenter 17 have a width slightly greater than the width of indenter 2 with respect to the right-left direction in the figure (with respect to a direction intersecting the direction of extension in a rod-like manner), and have a width that allows rod-like indenter 2 to bounce along the inner wall of hole portion for bouncing indenter 17. Indenter 2 is disposed such that the extending portion of rod-like portion 2a is along the inner wall of hole portion for bouncing indenter 17 (such that rod-like portion 2a extends along the vertical direction).

Hole portion for sliding load applying plate 18 extends along the right-left direction in the figure, that is, the horizontal direction, thus intersecting (for example, being orthogonal to) hole portion for bouncing indenter 17. Disposed in hole portion for sliding load applying plate 18 is load applying plate 3, which can move within hole portion for sliding load applying plate 18 along the horizontal direction in which it extends.

One end portion of hole portion for sliding load applying plate 18 with respect to its extension direction serves as an end wall surface 18a formed within the body of indenter pressing jig 16, and the other opposite end portion serves as an opening at the right end portion in the figure of the body of indenter pressing jig 16. Hole portion for sliding load applying plate 18, which intersects hole portion for bouncing indenter 17 as described above, is divided into a first region 18b to the left of intersected hole portion for bouncing indenter 17 (closer to end wall surface 18a) in the figure, and a second region 18c to the right of intersected hole portion for bouncing indenter 17 in the figure.

Load applying plate 3 has an opening forming portion 3a and an indenter pressing portion 3b. Opening forming portion 3a is a region provided with an opening for releasing and causing indenter 2 to bounce upward when this portion enters hole portion for bouncing indenter 17. Indenter pressing portion 3b is a region capable of closing hole portion for bouncing indenter 17 so as to press indenter 2 downward when this portion enters hole portion for bouncing indenter 17.

Each of two springs 10 has one end, for example, fixed to end wall surface 18a of hole portion for sliding load applying plate 18, and has the other end fixed to the left end portion in the figure of opening forming portion 3a of load applying plate 3.

In FIG. 22(a), stopper 11 has descended to block a region to the right of second region 18, thus pushing load applying plate 3 leftward. Accordingly, springs 10 have contracted to the fullest extent, with load applying plate 3 being disposed at the leftmost position. Stopper 11 fixes load applying plate 3 to the left position in the figure so as to prevent this plate from extending and moving rightward by a repulsive force due to the elastic force of springs 10.

At this time, opening forming portion 3a of load applying plate 3 is housed in first region 18b, while indenter pressing portion 3b is housed in hole portion for bouncing indenter 17 and second region 18c (to the left of stopper 11). At this time, therefore, indenter 2 is disposed below indenter pressing portion 3b (hole portion for sliding load applying plate 18) in hole portion for bouncing indenter 17, while being placed on the top surface of resin shock absorber 1.

Referring to FIG. 22(b), the entire indenter pressing jig 16 descends while stopper 11 keeps pushing load applying plate 3 leftward as in FIG. 22(a). As a result, in hole portion for bouncing indenter 17, indenter pressing portion 3b of load applying plate 3 included in indenter pressing jig 16 makes contact with indenter 2 therebelow and applies a load of pressing indenter 2 downward. Load applying plate 3 further moves downward while being in contact with indenter 2 in this manner, causing indenter 2 in contact therewith to be pressed into resin shock absorber 1 therebelow.

Referring to FIG. 22(c), stopper 11 is removed so as to move upward while indenter 2 is maintained in a downward-pressed state. If springs 10 extend rightward at this time by the elastic force, load applying plate 3 moves to the right of the figure, causing an opening in opening forming portion 3a (portion where a plate-like member is not disposed) to be located directly above indenter 2 in hole portion for bouncing indenter 17. In other words, the opening in opening forming portion 3a of load applying plate 3 releases the downward load that has been applied to indenter 2 by indenter pressing portion 3b until that time.

As a result, indenter 2 bounces upward by a repulsive force resulting from being pressed downward.

Inspection apparatus 500 is different from inspection apparatuses 100 to 400 only in that it has indenter pressing jig 16 as the load applying mechanism as described above, and is otherwise substantially the same in configuration as inspection apparatuses 100 to 400. Hence, the same elements are designated by the same signs and the description thereof will not be repeated. Specifically, although the illustration of the remaining apparatus body and the measuring mechanism forming inspection apparatus 500 is omitted in FIG. 22, any of inspection apparatuses 100 to 400 of the first to fourth embodiments may be used for this portion. That is, any of the measurement methods of the first to fourth embodiments can be used as the measurement method of this embodiment. Although not illustrated, indenter pressing jig 16 is grasped by linear guide 7 making contact with and fixed to struts 5, for example, of the apparatus body (for example, like load applying plate 3 of the first embodiment), and can move along the direction in which struts 5 extend (along the vertical direction).

The function and effect of this embodiment will now be described.

In this embodiment, indenter 2 having rod-like portion 2a extending in a rod-like manner is caused to bounce upward while being disposed so as to extend along the inner wall of hole portion for bouncing indenter 17. Thus, by setting particularly the width of the inner wall of hole portion for bouncing indenter 17 to be close to the width intersecting the direction in which rod-like portion 2a of indenter 2 extends (to be somewhat small), indenter 2 will reliably bounce upward along the vertical direction. This can reduce the possibility of compromising the reliability of a measurement result caused by indenter 2 bouncing in an oblique direction, for example, rather than bouncing in the vertical direction.

From this point of view, the inspection may be performed by inspection apparatus 500 having indenter pressing jig 16 of this embodiment, by using indenter 2 as a spherical object in the first to fourth embodiments. By so doing, even when indenter 2 as a spherical object is used, indenter 2 can reliably bounce in the vertical direction along the inner wall of hole portion for bouncing indenter 17, thereby improving the reliability of a measurement result.

In addition, since indenter 2 with rod-like portion 2a has spherical portion 2b or polyhedron shape portion 2c, by bringing the portion into contact with, and causing the portion to dig into, the top surface of resin shock absorber 1, damage to the surface of resin shock absorber 1 can be prevented when the portion is pressed into resin shock absorber 1.

Furthermore, since indenter 2 has rod-like portion 2a, the risk of a loss can also be reduced as compared to when indenter 2 is a spherical object.

The technical features in the respective embodiments described above can be combined and used as appropriate to such an extent that does not cause any technical contradictions.

It should be understood that the embodiments disclosed herein are illustrative and non-restrictive in every respect. The scope of the present invention is defined by the terms of the claims, rather than the description above, and is intended to include any modifications within the scope and meaning equivalent to the terms of the claims.

REFERENCE SIGNS LIST

1 resin shock absorber; 2 indenter; 2a rod-like portion; 2b spherical portion; 2c polyhedron shape portion; 3 load applying plate; 3a opening forming portion; 3b indenter pressing portion; 4 base; 5 strut; 6 shock absorber fixing plate; 6a first fixing region; 6b second fixing region; 7 linear guide; 8 height display plate; 8a scale; 9 spring fixing plate; 10 spring; 11 stopper; 12 height reference plate; 13 load detector; 14 ceiling portion; 15 speed measurement device; 16 indenter pressing jig; 17 hole portion for bouncing indenter; 18 hole portion for sliding load applying plate; 18a end wall surface; 18b first region; 18c second region; 100, 200, 300, 400, 500 inspection apparatus.

The invention claimed is:

1. A method for inspecting a resin shock absorber, comprising the steps of:
    pressing an indenter into a resin shock absorber for an elevator;
    releasing a load of pressing the indenter into the resin shock absorber;
    measuring a physical property value indicative of a repulsive force that causes the indenter to bounce from the resin shock absorber by the step of releasing a load; and
    determining necessity of replacement of the resin shock absorber by comparing a result of the physical property value obtained by the step of measuring a physical property with a reference value prepared in advance.

2. The method for inspecting a resin shock absorber according to claim 1, wherein
    in the step of measuring a physical property value, a height from the resin shock absorber that is reached by the bouncing indenter is measured.

3. The method for inspecting a resin shock absorber according to claim 1, wherein
    in the step of measuring a physical property value, it is detected whether or not a height reached by the indenter bouncing by the step of releasing a load reaches a height reference plate provided at a position of the reference value, and
    in the step of determining necessity of replacement, it is determined that the resin shock absorber needs to be replaced when the indenter does not reach the height reference plate.

4. The method for inspecting a resin shock absorber according to claim 1, wherein
    in the step of measuring a physical property value, a load when the indenter collides with a load detection device provided on a trajectory of the bouncing indenter is measured.

5. The method for inspecting a resin shock absorber according to claim 1, wherein
    in the step of measuring a physical property value a speed of the bouncing indenter is measured.

6. The method for inspecting a resin shock absorber according to claim 1, further comprising the steps of:
    by performing a step of measuring a deceleration of an elevator car when causing the car to collide with the resin shock absorber at a movable speed of the car, and a step of measuring the physical property value by pressing the indenter, for a plurality of times while varying a period of use of the resin shock absorber, determining a replacement time point when the deceleration obtained by the step of measuring a deceleration reaches a value at which the resin shock absorber should be replaced; and
    determining, as the reference value which is obtained from the indenter and at which the resin shock absorber should be replaced, the physical property value obtained by performing the step of measuring the physical property value by pressing the indenter at the replacement time point.

7. The method for inspecting a resin shock absorber according to claim 1, wherein
    the step of pressing an indenter is performed by a load applying mechanism moving downward along a strut extending along a direction in which the indenter bounces while making contact with the indenter, and
    the step of releasing a load is performed by the load applying mechanism moving in a horizontal direction along a linear guide extending along the horizontal direction, the horizontal direction intersecting the direction in which the indenter bounces.

8. An apparatus for inspecting a resin shock absorber, comprising:
    an apparatus body including a fixing mechanism for fixing a relative position of a resin shock absorber for an elevator;
    a load applying mechanism capable of applying a load of pressing an indenter into the resin shock absorber, and releasing the load; and
    a measuring mechanism to measure a physical property value indicative of a repulsive force that causes the indenter to bounce from the resin shock absorber upon release of the load,
    wherein the apparatus body includes
    a base on which the resin shock absorber is placed,
    a strut fixed to the base and extending along a direction in which the indenter bounces, and
    a linear guide fixed to the strut and extending in a horizontal direction intersecting the direction in which the indenter bounces, the linear guide being able to move the load applying mechanism in the horizontal direction, wherein
    the indenter can be pressed into the resin shock absorber by the load applying mechanism moving along the strut, and
    the indenter can be released from the resin shock absorber by the load applying mechanism moving in the direction in which the linear guide extends.

9. The apparatus for inspecting a resin shock absorber according to claim 8, wherein the indenter is made of metal, and has a spherical shape or polyhedron shape.

10. The apparatus for inspecting a resin shock absorber according to claim 8, wherein
the indenter is made of metal, and has the shape of an extending rod, and
the indenter has a spherical shape or polyhedron shape at one of end portions with respect to a direction in which the shape of an extending rod extends.

11. The apparatus for inspecting a resin shock absorber according to claim 8, wherein
the measuring mechanism is a height display plate to measure a height from the resin shock absorber that is reached by the bouncing indenter as the physical property value.

12. The apparatus for inspecting a resin shock absorber according to claim 8, wherein
the measuring mechanism is a height reference plate, provided at a position of a reference value of height reached by the bouncing indenter, of the apparatus for inspecting a resin shock absorber.

13. The apparatus for inspecting a resin shock absorber according to claim 8, wherein
the measuring mechanism is a load detector to measure, as the physical property value, a collision load of the indenter with respect to the measuring mechanism by receiving collision of the bouncing indenter.

14. The apparatus for inspecting a resin shock absorber according to claim 8, wherein
the measuring mechanism is a speed measurement device to measure a speed of the bouncing indenter as the physical property value.

15. The apparatus for inspecting a resin shock absorber according to claim 8, wherein
the fixing mechanism holds down and fixes, by being fixed to the strut, the resin shock absorber placed on the base, and
the fixing mechanism can pinch and fix the resin shock absorber by a first fixing region disposed with respect to the direction of the resin shock absorber in which the indenter bounces and a second fixing region intersecting the first fixing region and disposed at a side surface of the resin shock absorber.

16. The apparatus for inspecting a resin shock absorber according to claim 8, wherein
the load applying mechanism further includes an indenter pressing jig having an inner wall extending along the direction in which the indenter bounces.

* * * * *